United States Patent [19]
Dalton et al.

[11] Patent Number: 5,637,463
[45] Date of Patent: Jun. 10, 1997

[54] METHOD TO DETECT PROTEIN-PROTEIN INTERACTIONS

[75] Inventors: Stephen Dalton, Bloomfield; Jarema P. Kochan, Verona; Mark A. Osborne, South Brunswick, all of N.J.

[73] Assignee: Hoffmann-La Roche Inc., Nutley, N.J.

[21] Appl. No.: 434,730

[22] Filed: May 4, 1995

[51] Int. Cl.$^6$ ................ C12Q 1/08; C12P 21/00; C07K 1/00; C07H 21/04
[52] U.S. Cl. ............ 435/6; 435/697; 435/172.1; 435/320.1; 530/350; 536/23.01; 536/23.5
[58] Field of Search .................. 435/6, 7.21, 7.31, 435/69.1, 69.7, 172.1, 172.3, 320.1; 536/23.4, 23.5, 23.74; 530/350

[56] References Cited

U.S. PATENT DOCUMENTS 5,283,173  2/1994  Fields et al. .................. 435/6
5,503,977  4/1996  Johnsson et al. ............. 435/6

FOREIGN PATENT DOCUMENTS

92/05286  4/1992  WIPO .
94/10300  5/1994  WIPO .

OTHER PUBLICATIONS

Luban et al. The yeast two–hybrid system for studying protein–protein interactions Current Opinion in Biotechnology vol. 6 59–64 1995.

Keegan et al., Science 231:699–704 (1986).
Curran et al., Cell, 55:395–397 (1988).
McKnight et al., Proc. Natl. Acad. Sci. USA, 84:7061–7065 (1987).
Paolini, R., et al., J. Exp. Med. 181:247–255 (1995).
Kihara, H., et al., J. Biol. Chem., 269:22427–22432 (1994).
Shiue, L., et al., Mol. Cell. Biol., 15:272–281 (1995).
Brent & Ptashne, Cell, 43:729–736 (1985).
Dalton and Treisman, Cell, 68:597–612 (1992).
Fields and Sternglanz, Trends Genet., 10:286–292 (1994).

*Primary Examiner*—James Ketter
*Assistant Examiner*—John S. Brusca
*Attorney, Agent, or Firm*—George W. Johnston; Patricia S. Rocha-Tramaloni; Raina Semionow

[57] ABSTRACT

Methods are provided for studying protein-protein interactions which require posttranslational modification of one of the proteins. The interaction is detected by reconstituting the activity of a transcriptional activator. This activity is dependent on the interactions between three different proteins. These include two chimeric proteins, one of which must be posttranslationally modified by the activity of the third protein in order for the chimeric proteins to interact. One of the chimeric proteins contains a transcriptional activation domain fused to a test protein. The second chimeric protein contains a DNA-binding domain of a transcriptional activator fused to the other test protein.

20 Claims, 10 Drawing Sheets

FIG. 1 TRANSCRIPTIONAL ACTIVATION VIA THE SH2-PHOSPHOTYROSINE INTERACTION

A = CYC1 5' END + pGAL PROMOTER

B = HUMAN Lck (AMINO ACIDS 1-509)

C = CYC1 3' TERMINATION SIGNAL pGAL-lck (p4140)

Expression of tyrosine kinases increases phosphotyrosine

METHOD TO DETECT PROTEIN-PROTEIN INTERACTIONS

FIELD OF THE INVENTION

The present invention relates to a genetic method for the detection of protein-protein interactions that are dependent upon post-translational protein modifications. These protein interactions are detected by utilizing fusion proteins whose expression results in transcriptional activation.

BACKGROUND

Protein-protein interactions are responsible for key biological functions such as cell division and enzyme regulation and are involved, for example, in the assembly of enzyme subunits; in antigen-antibody reactions; in forming the supramolecular structures of ribosomes, filaments, and viruses; in molecular transport; and in the interaction of receptors on cell surfaces with growth factors and hormones. It is also through protein-protein interactions that oncogene expression results in neoplastic transformation. For example, some oncogenes encode protein kinases whose enzymatic activity on cellular target proteins leads to the cancerous state.

In addition to using well known biochemical techniques to study protein-protein interactions, a method for detecting protein-protein interactions using a genetic system is described in U.S. Pat. No. 5,283,173. This two hybrid genetic system is capable of detecting proteins that interact with a known protein, determining which domains of the proteins interact, and providing the genes for newly identified interacting proteins. The two hybrid system of the '173 patent detects protein-protein interactions using transcriptional activation of a reporter gene as an assay mechanism.

Transcription can be activated through the use of two functional domains of a transcription activation moiety: a domain or sequence of amino acids that recognizes and binds to a specific site or sequence of nucleotides on a target DNA, i.e. a reporter gene; and a domain (sequence of amino acids) that is capable of activating transcription of the DNA when physically associated with the DNA-binding domain and is necessary for activation of the target gene. See Keegan, et al., Science, 231, 669–704 (1986); Ma and Ptashne, Cell, 48, 847–853 (1987). The two functional domains may be derived from a single transcription activation protein. Alternatively, it has been shown that these two functions can also reside on separate proteins (McKnight et al. Proc. Natl. Acad. Sci. USA 89, 7061–7065 (1987); Curran et al. 55, 395–397 (1988). The transcription activation domains may also be derived from synthetic DNA-binding and transcription activation proteins.

Transcriptional activation has been studied, for example, using the Gal4 protein of the yeast *Saccharomyces cerevisiae*. The Gal4 protein is a single transcriptional activation protein required for the expression of genes encoding enzymes of galactose utilization (Johnston, Microbiol. Rev., 51,458–476 (1987). Such a system is well known. See U.S. Pat. No. 5,283,173.

A disadvantage of studying protein-protein interactions using certain host cells, such as yeast, for the two hybrid system is that interactions mediated by post-translational modifications, such as tyrosine phosphorylation, cannot be detected. Especially limiting has been the inability of such a two hybrid system to detect interactions which are dependent on specific post-translational modifications which are not employed by the host cell into which the hybrid genes have been introduced.

Accordingly, it is an object of the present invention to provide an improved genetic method for the detection of protein-protein interactions, especially those protein interactions requiring specific post-translational modifications, such as the phosphorylation of tyrosine residues which is a critical step in the signal transduction pathways of activated cell-surface receptors.

Another object of the invention is to provide the regulated expression of proteins involved in protein-protein interactions as it relates to this system.

It is a further object of the present invention to provide a method for identifying amino acid residues which are critical for protein-protein interactions to occur.

Another object of the present invention is to provide a method for the identification of novel proteins which can be post-translationally modified.

It is a further object of the present invention to provide a method for the identification of novel proteins which bind to post-translationally modified proteins.

Another object of the present invention is to provide a method of identifying novel proteins that can post-translationally modify other proteins.

It is a further object of the invention to provide a method for the identification of molecules which inhibit protein-protein interactions, as directed by proteins capable of post-translationally modifying other proteins, proteins capable of being post-translationally modified by other proteins or proteins capable of binding to post-translationally modified proteins.

SUMMARY OF THE INVENTION

The present invention provides reagents and methods for detecting protein-protein interactions which are dependent upon the post-translational modification of at least one of the proteins involved in the interaction by at least one other protein. The method utilizes a protein capable of post-translationally modifying another protein that is a hybrid or is endogenous to the host cell and wherein such modification is necessary for the interaction of the modified protein with another protein of interest. The protein interactions are detected by bringing together the separable domains of a transcriptional activation moiety to a target reporter gene thereby reconstituting the activity of a protein capable of activating transcription.

In a preferred embodiment, two hybrid genes are constructed which encode two hybrid proteins. The first hybrid protein contains a DNA-binding moiety fused to a first test protein that is capable of being post-translationally modified. The second hybrid protein contains a transcriptional activation moiety fused to a second test protein which will interact with the first test protein only when the first test protein has been post-translationally modified.

The hybrid proteins can be exchanged such that the second hybrid protein contains a transactivation domain of a transcription activator moiety fused to a test protein that is capable of being modified. The first hybrid protein contains the DNA-binding domain of a transcriptional activation moiety fused to a second test protein which will interact with the second test protein only when the second test protein has been post-translationally modified.

A third gene encoding a third test protein that is able to post-translationally modify the first test protein is also provided. The post-translational modification of the first test protein by the third test protein then enables the interaction between the first test protein and the second test protein. The protein-protein interaction between the first test protein and the second test protein brings the the DNA-binding moiety into sufficient proximity the transcriptional activation moiety to activate the transcription of the reporter gene. In the absence of post-translational modification of the first test protein by the third test protein, there is no transcriptional activation of the reporter gene, reflecting the lack of any interaction between the two hybrid proteins.

The expression of the three genes in the claimed method is tightly regulated so that no expression of the reporter gene is observed in the absence of transcriptional activation.

An example of the method of the present invention is depicted in FIG. 1. In FIG. 1, DB represents a DNA binding moiety, ACT represents a transcriptional activation moiety, Pro represents a promoter region, the star is the phosphorylated tyrosine residue.

This method can be utilized for the rapid screening of compounds, peptides or intact protein molecules which block transcriptional activation by their ability to block one of the key interactions between the proteins in the method. An inhibitor may block the activity of the third test protein, for example an enzyme such as protein tyrosine kinase, by inhibiting its activity, and thereby blocking post-translational modification of the first test protein. In addition, the interaction between the hybrid proteins, a post-translationally modified protein and its binding protein, could be blocked by an inhibitor.

BRIEF DESCRIPTION OF THE DRAWINGS

FIG. 7 shows the cDNA sequence of novel SH2 domain containing protein SH2-A identified with the disclosed method (SEQ. ID NO. 13).

FIG. 8 shows the cDNA sequence of novel SH2 domain containing protein SH2-B identified with the disclosed method (SEQ ID NO. 14).

DETAILED DESCRIPTION

Figure 1:
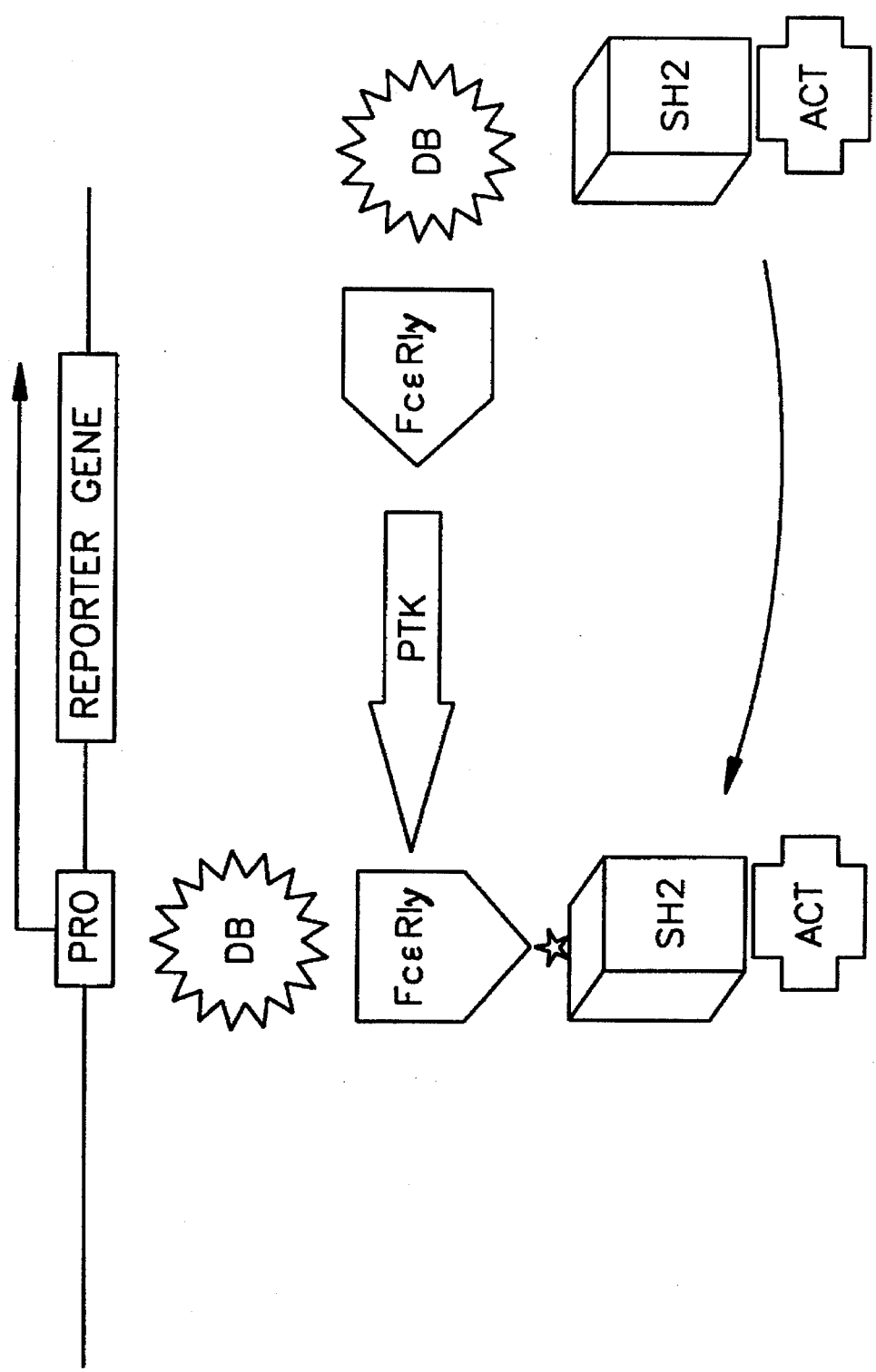
FIG. 1 schematically represents transcription of the detectable gene as described in the example.

The present invention provides a method for detecting an interaction between a first test protein and a second test protein, comprising:

(A) introducing into a host cell that contains a detectable gene which expresses a detectable protein when the detectable gene is transcribed, the following:
  (i) a first chimeric gene that is capable of being expressed in the host cell, said first chimeric gene encoding a first hybrid protein, said first hybrid protein comprising:
    (a) a DNA-binding moiety that recognizes a binding site on the detectable gene in the host cell; and
    (b) a first test protein or fragment thereof to be tested for interaction with a second test protein or fragment thereof, said first test protein being capable of interacting with a third test protein;
  (ii) a second chimeric gene that is capable of being expressed in the host cell, said second chimeric gene encoding a second hybrid protein, said second hybrid protein comprising:
    (a) a transcriptional activation moiety; and
    (b) a second test protein or fragment thereof to be tested for interaction with said first test protein or fragment thereof; and
  (iii) a third gene that is capable of being expressed in the host cell, said third gene comprising a DNA sequence that encodes a third test protein or fragment thereof which is capable of interacting with said first test protein;
wherein said first, second and third genes also contain an inducible promoter region such that expression of said genes in the host cell can be regulated;

(B) subjecting the host cell to conditions such that said first, second and third hybrid proteins are expressed in sufficient quantity for said third test protein to interact with said first test protein thereby enabling the interaction between said first test protein and said second test protein, which in turn results in the transcription of the detectable gene; and (C) determining whether the detectable gene has been transcribed, the transcription of the detectable gene being indicative of whether an interaction has occurred between said first and second test proteins.

More specifically, a method for the detection of protein-protein interactions which are dependent upon the post-translational modification of one of the proteins is provided in accordance with the present invention.

The method of the present invention utilizes separate DNAs which direct the regulatable expression of the key components of the protein-protein interaction system. Regularable expression is important since the unregulated expression of non-endogenous proteins in a host cell is typically toxic to the cell. For example, src expressed in yeast is known to be lethal to the cells. (See Kornbluth, S., et al., (1987) Proc. Natl. Acad. Sci. USA 84, 4455–4459.)

Regulation of expression is achieved in the present invention by fusing the DNA encoding the proteins of interest to an operator-promoter region that is normally completely turned off. The addition of a small molecule, such as galaclose for the galactose promoter, or IPTG for the β-galactosidase promoter, then results in the immediate stimulation of transcription resulting in the production of the protein encoded by the mRNA. (Johnston, M. (1987) Microbiological Reviews 51, 458–476). The expression of all three components is tightly regulated so that no expression is observed in the absence of transcriptional activation.

In the present invention the DNAs are introduced into a host cell and are capable of being expressed in the host cell in sufficient quantity for a reporter (sometimes also referred to as a "detectable") gene to be activated. The host cell may be any type of cell, including yeast, bacteria or mammalian cells. The preferred host cell is a yeast cell, most preferably Saccharomyces cerevisiae.

The host cell contains a reporter gene having a binding site for a DNA-binding domain such that the reporter gene product is a detectable protein when the reporter gene is transcriptionally activated. A reporter or detectable gene is one whose transcription is detectable and/or which expresses a protein which is also detectable, either of which can be assayed. Examples of readily detectable proteins include β-galactosidase, green fluorescent protein, luciferase, alkaline phosphatase and chloramphenicol acetyl transferase as well as enzymes or proteins, i.e. selectable markers, involved in nutrient biosynthesis such as Leu2, His3, Trp1, Lys2, Ade2 and Ura3. In a preferred embodiment, the reporter gene used is *E. coli* Lac Z which encodes β-galactosidase.

Activation occurs when a transcriptional activation moiety is brought into sufficient proximity to the DNA-binding moiety.

The DNA-binding moiety and the transcriptional activation moiety can be derived from a single transcriptional activator having separate DNA-binding and transcriptional activation domains, found, for example, in the yeast Gal4 and Gcn4 proteins. These functional moieties can also be synthetic. Preferably, the DNA-binding moiety and the transcriptional activation moiety are from different proteins. In a preferred embodiment of the present invention, the DNA-binding domain is derived from the *E. coli* protein LexA and the transcriptional activation domain is derived from the transcriptional activator of Herpes Simplex Virus Type I Vmw65 protein.

In the present method, a first chimeric gene is provided which is capable of being expressed in the host cell. The first chimeric gene is introduced into the host cell in the form of a plasmid or a DNA stably incorporated into the genome of the host cell, or by other known methods (Schiestl, R. H. and Gietz, R. D. (1989) Curr. Genet. 16:339–346 and Guthrie, C. and Fink, G. R. (1991) Meth. Enz. 194:1–933.)

The first chimetic gene comprises a DNA sequence that encodes a first hybrid protein. The first hybrid protein contains a DNA-binding domain that recognizes the binding site on the detectable gene in the host cell. The first hybrid protein also contains a first test protein or protein fragment which is fused to the DNA binding moiety. The first test protein is the protein, or fragment thereof, to be tested for interaction with a second test protein or protein fragment.

In one embodiment, the first test protein is capable of being post-translationally modified by a third protein, for example an enzyme, such modification being required for a protein-protein interaction to take place between the first test protein and a second test protein.

In the present method, a second chimeric gene is also provided which is capable of being expressed in the host cell. The second chimeric gene is introduced into the host cell using techniques known in the art. The second chimeric gene contains a DNA sequence that encodes a second hybrid protein containing a transcriptional activation domain. The second hybrid protein also contains a second test protein or a protein fragment which is fused to the transcriptional activation moiety. In this embodiment, it is the interaction between the first test protein and the second test protein that is of interest and subject to detection. This interaction in this embodiment is dependent upon the successful post-translational modification of the first test protein by a third test protein described below.

A third gene, which may or may not be a hybrid gene, is also provided which is capable of being expressed in the host cell. The third gene encodes a third test protein that interacts with the first test protein. In one embodiment, the third test protein is an enzyme that can post-translationally modify the first test protein, thus enabling the interaction between the first test protein and the second test protein.

Depending upon the number of interdependent protein-protein interactions being studied, any number of genes can be introduced into a host cell that is capable of expressing the proteins involved in an interaction mechanism under study.

In an alternate embodiment, two proteins must interact to facilitate the interaction with a third protein. In yet another embodiment, the third gene may also encode a protein which, upon interaction with one of the other proteins, effects an allosteric change necessary for the other proteins to interact. In an alternate embodiment a protein must interact with a small molecular weight compound to facilitate the interaction with a second protein. The third gene may encode a protein which upon interacting with a precursor of the small molecular weight compound, enzymatically converts it to the small molecular weight compound. This compound interacts with the first protein, effecting an allosteric change necessary for the second protein to interact.

The interaction between the first test protein and the second test protein in the host cell brings the DNA-binding moiety into sufficient proximity to the transcriptional activation moiety to activate the transcription of the reporter gene. In the absence of post-translational modification of the first test protein, there is no transcriptional activation, reflecting the lack of an interaction between the first and second test proteins.

The method is carried out by introducing the first chimeric gene, the second chimeric gene and the third gene into the host cell. This can be done in any order. The host cell is subjected to conditions under which all the proteins are expressed simultaneously and in sufficient quantity for the detectable gene to be activated and express a detectable protein. The cells are then tested for their level of expression of the detectable protein in comparison to the level of expression in the absence of an interaction between the test proteins. When there is an interaction, the expression level is greater than when there is not an interaction.

The method of the present invention can be utilized to detect interactions between proteins which are dependent on the presence of post-translational modifications. These modifications include, but are not limited to, serine/threonine phosphorylation, fatty acid acylation, various forms of glycosylation, ADP-ribosylation and myristylation which may not naturally occur in the host cell. Alternatively, an engodenous post-translational modification activity could be altered as to more effectively modify the test protein(s). This can be accomplished by inserting appropriate protein sorting information into the modification protein.

One post-translational modification, phosphorylation of tyrosine residues, is a critical step in the signal transduction pathway of activated cell surface receptors. Signal transduction via immunologically important receptors, for example, the high affinity IgE receptor, FceRI, or the T cell receptor, is mediated by subunits which contain immunoreceptor tyrosine-based activation motifs (ITAM). (Cambier, J. C., Imm. Tod, 16, 110 (1995)). These motifs are phosphorylated by tyrosine kinases, which subsequently permits their interaction with src-homology 2 (SH2)-containing proteins, leading to cellular activation. For the FceRI, this activation causes increases in intracellular calcium, diacylglycerol and inositol triphosphate metabolism, as well as histamine and arachidonic release (Beaven, M. A., Metzger, H. Imm. Tod. 14, 222 (1993))

In one embodiment of the present method, the first hybrid protein contains the DNA-binding domain of a transcriptional activator fused to a tyrosine motif-containing protein, for example, the FeeRIβ or γ polypeptides, or the T cell receptor ζ chain. A second hybrid protein contains a transcriptional activation domain of a transcriptional activator fused to an SH2 domain of a known protein, for example Syk or Lyn. An SH2 domain requires phosphorylation of a tyrosine containing protein in order to bind to the tyrosine-containing protein. The third protein is a protein tyrosine kinase, PTK, which is encoded by the third gene. This PTK, for example, Lck or Lyn, is able to phosphorylate the tyrosine residues of the tyrosine containing protein, thereby enabling the interaction with an SH2 protein. Each of the proteins may comprise the complete protein or a functional region of the complete protein. In the absence of phosphorylation, there is no transcriptional activation thereby reflecting the lack of any interaction between the tyrosine-motif containing protein and the SH2 protein.

In a preferred embodiment, the first plasmid includes the cDNA of the FceRIγ subunit cytoplasmic tail (CT), which encodes an ITAM, fused to the DNA encoding the bacterial DNA binding protein LexA. The second plasmid includes SH2 domains of the protein tyrosine kinase (PTK) Syk, which have been demonstrated to bind to the FceRIγ (R. Paolini, et al., J. Exp.Med. 181,247(1995); H. Kihara, et al., J. Biol Chem. 269, 22427(1994); L. Shiue, et al., Mol. Cell. Biol. 15:1, 272 (1995)), joined with the HSV1 Vmw65 protein transcriptional activation region. The PTKs Lck and Lyn were independently introduced into the third plasmid, in order to phosphorylate the LexA-FceRIγ CT ITAM. All three plasmids contain a galactose-inducible promoter such that in yeast cells containing any of the plasmids, expression of the gene products is repressed on glucose-containing medium and induced on galactose-containing medium.

Also contemplated as a part of the present invention is a kit for the detection of interactions between test proteins. The kit includes, for example, three or more DNA sequences which include a plasmid comprising a sequence that directs the expression of a DNA binding moiety fused to a sequence directing the expression of a first protein of interest; a plasmid comprising a sequence directing the expression of a transcriptional activation moiety fused to cloning sites for a eDNA library or specific protein fusions; a plasmid comprising a sequence directing the expression of protein modification activity; and a plasmid comprising a reporter gene. The sequences can be borne on one or more plasmids or episomes, or integrated into the genome or transiently introduced into the host cell.

The method of the present invention can be utilized for the rapid screening and identification of molecules, peptides or proteins as measured by their ability to block the activity of the PTK by inhibiting the enzymatic activity, or by their ability to block the interaction between phospho-tyrosine binding proteins, such as SH2 proteins and the tyrosine-containing region of a protein capable of being phosphorylated. Other phospho-tyrosine binding proteins are known. (Bork and Margolis, Cell 80:693–694 (1995); Kavanaugh and Williams, Science 266:1862–1865 (1994); and Gustafson et at., Mol. Cell Biol., 15:2500–2508 (1995).

Various known proteins which comprise the components of the detection system of the present invention, i.e. the DNA-binding moiety, the transactivation moiety, the PTK, the tyrosine-containing protein and the SH2 protein, may be substituted to identify inhibitors of the protein interactions.

For example, the identity of the reaction which is blocked can be determined by substituting different PTKs to determine if different PTKs are inhibited to the same or different extents. In a similar manner, various SH2 proteins or tyrosine-containing regions which can be phosphorylated can be substituted to ascertain if the interaction between these different proteins is also blocked by a specific molecule, peptide or compound. In this manner, both the target protein, as well as the specificity of the inhibitor can be established.

The method of the present invention can also be utilized to screen for compounds which inhibit tyrosine kinases which phosphorylate tyrosine residues. Tyrosine phosphorylation is essential to facilitate the interaction of tyrosine containing proteins with SH2 containing proteins. Alternatively, the interaction between SH2 proteins and phosphotyrosine proteins can be blocked. When these interactions are blocked, there is no activation of the LacZ reporter gene which expresses g-galactosidase and therefore no β-galactosidase will be detected. Compounds which block the synthesis of β-galactosidase can be tested for their specificity by examining their activity in non-tyrosine kinase dependent interactions, or in other PTK reactions in which the specificity of the interacting components has been changed by introducing different PTKs, different SH2 proteins, or proteins containing different tyrosine-containing regions that can be phosphorylated. Compounds which block only specific PTKs or interacting components are deemed to be specific.

In addition, interactions between a first test protein and a library of proteins can be tested. For example, the first test protein may be derived from a bacterial protein, a viral protein, an oncogene-encoded protein, a growth factor or an enzyme. The second test protein may be derived from a cDNA library of plasmids or DNA as described above. The third test protein may be derived from DNA encoding a post-translational enzyme, or another component of the complex. Thus, novel proteins which comprise the components of the system also may be isolated.

In a preferred embodiment, a DNA fragment encoding a tyrosine-containing region of a protein that can be phosphorylated, i.e. an ITAM FceRIγ or FceRIβ, is fused to LexA, and introduced into yeast cells carrying a reporter gene and a PTK. A library of the second hybrid gene, which contains the Vmw65 activation domain fused to DNA fragments obtained from any cell line, tissue mRNA or other DNA (including DNA that encodes random peptides) which encodes proteins, is constructed and introduced into cells carrying the first hybrid. If any of the hybrid genes from the library is able to interact with the phospho-tyrosine region containing protein, transcription of the reporter gene occurs. This hybrid gene can be isolated, and the novel protein and/or gene encoding therefore characterized by methods known in the art.

In a similar manner, novel proteins containing tyrosine residues which can be phosphorylated by different PTKs and that can interact with different SH2 proteins can be readily isolated and characterized. Novel PTKs can be isolated by inserting cDNA fragments into a vector and introducing the library of cDNAs into cell lines which carry only the two hybrid genes. In the absence of tyrosine phosphorylation there is no transactivation. However, if any of the cDNAs encodes a PTK, there is transcription of the reporter gene. The novel cDNA encoding the novel PTK can be isolated and characterized.

The present invention further provides a method of identifying compounds or peptides having therapeutic use in the areas of oncology and cardiovascular, inflammatory and metabolic diseases. The present invention has utility in any disease process that is regulated by tyrosine phosphorylation and the subsequent interactions which occur when phosphotyrosine binding proteins, such as SH2 containing proteins, bind to a phosphotyrosine motif.

The present invention further provides novel SH2 proteins which are useful in screening inhibitors of mast cell activation, a process which is a critical factor in IgE mediated allergic response.

The following example further illustrates the various features of the invention, and is not intended in any way to limit the scope of the invention which is defined by the claims.

EXAMPLE

Plasmid Constructions

In order to detect protein-protein interactions, three plasmids were constructed. The first directed the inducible synthesis of a chimetic protein which consisted of a DNA-binding moiety covalently linked to the protein of interest, the 42 amino acids of the cytoplasmically disposed (cytoplasmic tail CT) gamma (γ) subunit of human FceRI (FceRIγCT). (Kuster, H., et al., (1990) J. Biol. Chem. 265, 6448-6452). The DNA binding moiety, the *E. coli* LexA protein (Brent & Ptashne (1985) Cell 43:729-36) binds to its cognate operator sequence, the Lex A operator (Brent & Ptashne (1981) Proc. Natl. Acad. Sci. USA, 78:4204-8.) The plasmid, p4108, was constructed, using common techniques known by those skilled in the art, to insure that the protein was made only when induced, and would be transported into the nucleus where it will bind to the LexA operator. This first hybrid gene encoded a fusion protein consisting of the *E. coli* LexA protein, a nuclear localization sequence, and the 42 amino acids of the FceRIγCT and was constructed with the specific intent to allow other genes to be cloned in-frame with LexA in order to identify protein-protein interactions with this system. The plasmid included the inducible yeast promoter, pGAL1-10. In yeast cells, the plasmid, which was maintained in medium lacking tryptophan, directed the synthesis of a LexA-NLS-FceRIγ CT fusion protein when the cells were grown in the presence of galactose, but not when cells were grown in the presence of glucose.

Plasmid 4108 was constructed using the yeast plasmid YLexA. YLexA is a derivative of pSD04a and contains a galactose-inducible promoter and transcription initiation and termination sequences from the yeast CYC1 gene (Dalton and Treisman, Cell 68, 597-612, 1992). The gene for the *E. coli* protein LexA (amino acids 1-202), and restriction sites for cloning other genes in-frame were inserted into the multiple cloning site. YlexA was digested with Eco RI and SpeI and a PCR fragment encoding the 42 amino acid C-terminus of the human gamma subunit of the high affinity IgE receptor FceRIγ (Kuster et al. 1990 JBC 265:6448-6452) was cloned in to make p3847. The PCR primers used were: 5'-GGCATCCAGGCGGCCGCG AATTCTCGACTGAAGATCCAAGTGCGA-3' (SEQ ID NO:1) and 5'-GGCACTAGTCTACTGTGGTGGTTTCTC (SEQ ID NO:2). The first primer included a NotI site (underlined nucleotides) and an Eco RI site (nucleotides in BOLD lettering) in addition to a sequence corresponding to the cytoplasmic tail of the human FceRIγCT. The second primer contained a SpeI restriction site (underlined) for cloning into the vector and a stop codon (BOLD) in addition to the sequence corresponding to the 3' end of FceRIγCT.

Plasmid 3847 was generated and its sequence confirmed, then digested with Not I and Eco RI. Annealed oligonucleotides corresponding to the nuclear localization sequence of SV40 T antigen (Kalderon, D., et al. (1984) Cell 39: 499-509), were inserted as a Not I/Eco RI fragment. The sequence of the oligonucleotides were: 5'-GGCCGCGCCAAAGAAGAAGAGAAAGGTAGCG-3' (SEQ ID NO:3) and 5'-AATTCGCTACCTFTCT CTTCTTCTTTGGCGC-3' (SEQ ID NO:4). The insertion of the oligonucleotides was confirmed by DNA sequencing.

Figure 2:
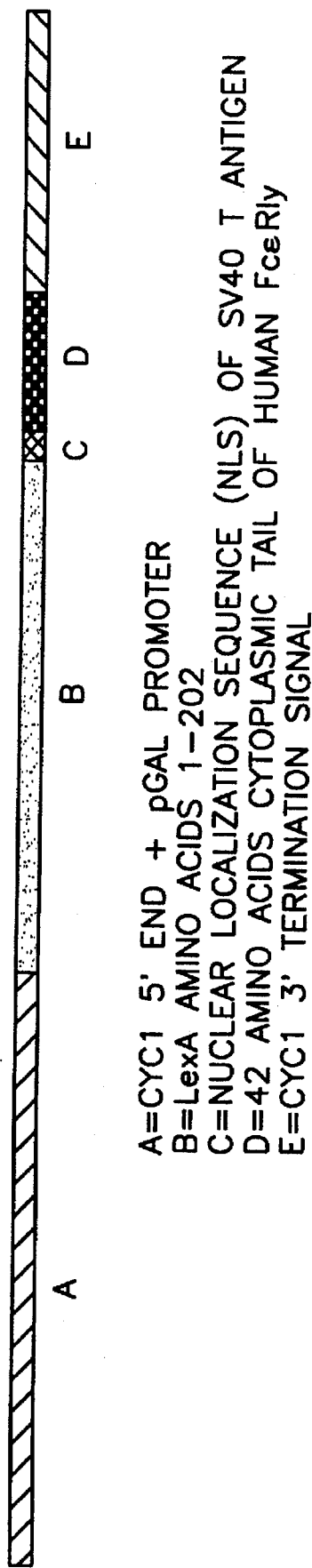
FIG. 2 schematically represents the plasmid construct YlexA-FcεRIγCT.

FIG. 2 illustrates the LexA-FceRIγCT plasmid.

To provide another ITAM to compare to LexA-γCT in the protein-protein interaction system, another plasmid, pLexA-βCT, was constructed. The C-terminus of the rat 13 subunit of FceRI (Kinet, et al. 1988 Proc. Natl. Acad. Sci. 85:6483-6487) was PCR amplified and subcloned into p4108 RI/SpeI. Expression was confirmed by anti-LexA immunoblotting. Antibodies to the glutathione-S transferase fusion protein were made by immunizing rabbits with purified LexA protein made in the plasmid pGe3x (Pharmacia, Piscataway, N.J.).

A second plasmid constructed was p4064. In yeast cells, this plasmid, which was maintained in media lacking uracil, directed the galactose-inducible expression of a covalently-linked fusion protein between the HSV1 VMw65 transcriptional activation region and any gene cloned into the multiple cloning site. An NLS directed the fusion protein to the nucleus, and the 9E10 epitope tag allowed for detection of the fusion protein with a commonly available antibody 9E10 (American Type Culture Association, ATCC).

The plasmid 4064 is a derivative of pSD10a (Dalton and Treisman, 1992) containing the SV40 T NLS (Kalderon et al, 1984) and the 9E10 c-myc epitope tag (Evan, G. I., et al. (1985) Mol. Cell. Biol. 5:3610-3616) cloned into the Bam HI-Sal I site of SD10a. pSD10a was digested with Bam HI and Sal I, and annealed oligonucleotides corresponding to the SV40 T antigen NLS (Kalderon et al, 1984) and the 9E10 c-myc epitope (Evan, et al, 1985) were inserted. The sequence of the oligonucleotides was: 5'-GATCCCCAAA GAAGAAGAGAAAGGTAGAGCAGAAGCT-GATTAGCGAGGA AGATCTGAATGCG-3' (SEQ ID NO:5) and 5'-TCGACGCATTCAGATCTTCCTCGCT AATCAGCTTCCETACCTTTCTCTTCT TCTTTGGG-3' (SEQ ID NO:6). The order of the elements of the plasmid was pGAL-ATG-NLS-cMyc-Vmw65-BstXI-stuffer-BstXI-STOP-CYC1 3'. This plasmid was used to generate the cDNA library from RBL-2H3 cells and was utilized for the fusions with the SH2 domains.

Figure 3:
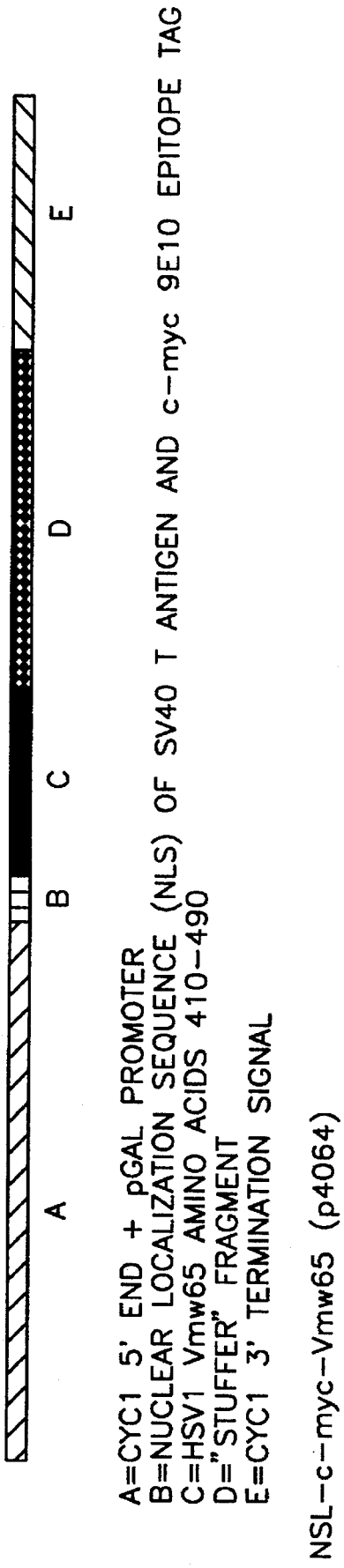
FIG. 3 schematically represents the plasmid construct NLS-c-myc-Vmw65.

FIG. 3 illustrates the Vmw65 fusion plasmid.

A third plasmid, p4140, was constructed to direct the synthesis of a protein kinase in yeast cells. This plasmid directed the expression of the human Lck protein (Perimutter et al, J. Cell Biochem. 38:117-126, 1988) from the pGAL promoter. Both the full-length Lck cDNA and the cDNA encoding the kinase domain alone were PCR amplified from the plasmid p56 (a gift of P. Bum, Roche) and inserted in between the EcoRI and Xba I sites of pSD04b (Dalton and Treisman, 1992) to generate p4125 and p4131, respectively. The entire multiple cloning site region was removed to pRS415 (Strategene Cloning Systems, La Jolla, Calif.) so that the yeast selectable marker would be LEU2 (yeast will carry this plasmid if grown in the absence of added leucine). The plasmids 4140 (Lck) and 4141 (kinase domain) were used to clone genes for other protein tyrosine kinases. For example, the entire human Lyn cDNA (a gift of B. Repetto, Roche) was PCR amplified and inserted into p4140. The sequences of all plasmids were confirmed and expression of the proteins verifed by anti-phosphotyrosine immunoblotting and/or detection by specific antibodies. These plasmids were used to direct the expression of each protein tyrosine kinase individually in yeast cells.

Figure 4:
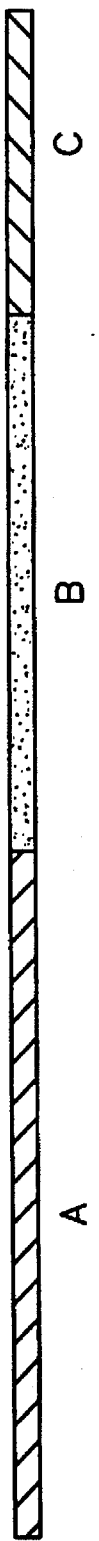
FIG. 4 schematically represents the plasmid construct pGAL-Lck.

FIG. 4 illustrates the Lck plasmid.

Construction of the cDNA Library

In order to identify novel proteins that interact with the tyrosine-phosphorylated LexA-FceRIγCT, a cDNA library was constructed from RBL-2H3 cells, a mast cell line which expressed FceRI. This library was prepared by standard techniques (Gubler and Hoffmann, 1983 Gene 25:263-269). mRNA was then prepared according to manufacturer's instructions (Pharmacia mRNA purification kit). 2 μg of mRNA was used to synthesize cDNA essentially as described by Gibco-BRL (Superscript kit), with modifications. (The eDNA was primed by both oligo-dT and random hexamers.) The eDNA was linkered with phosphorylated BstXI adaptors 5'-CTCTAAAG-3' and 5'-CTTTAGTGCACA-3' (SEQ ID NO:12) and fractionated by Sephacryl S-500 chromatography. Fractions were collected and cDNA larger than 1.0 kb was pooled, concentrated, and ligated to p4064 which was cut with BstXI. Ligations were transformed into Electromax electrocompletent *E. coli* DH10b (GIBCO-BRL) by electroporation. Approximately 5 million clones were obtained.

Screening the Library

To identify novel cDNAs encoding proteins which interact with LexA-FceRIγCT, a reporter yeast strain was constructed using standard methods (Meth. Enz. 194, 1991 entire volume). Yeast strain S-260 (MATα his3-11,15 trp1-1 ade2-1 leu2-3,112 ura3::LexOp-LacZ ho can1-100) contains four ColE1 operators 5' to the *E. coli* LacZ gene integrated at the URA3 locus in *S. cerevisiae*. The plasmid encoding the LexA-FceRIγCT fusion 4108 and the Lck plasmid 4140 were introduced into S-260. One colony was selected and grown in SC-Trp-Leu liquid media and transformed with the library plasmid DNA as described (Sheistl and Geitz 1989, Dalton and Treisman 1992, supra). Two separate transformations were done, with a total of 500,000 transformants screened. Transformants were selected and screened as described in Dalton and Treisman, 1992. 50 positive colonies were identified, purified, and tested for the requirement of Lck for β-galactosidase activity. Of the 50, 5 required Lck. These were rescued in *E. coli* strain KC8 (gift of P. Silver, Harvard Medical School, Dana Farber Cancer Inst.) and their DNA sequence identified.

Two unique cDNAs, SH2-A and SH2-B, were identified which encoded novel open reading frames (ORFs) that contain SH2 domains (Pawson, T. (1995) Nature (Lond.) 373:573–580). Of the five plasmids that were identified, three plasmids were derivatives of the same eDNA encoding novel protein SH2-A. The two other plasmids contained overlapping sequences that encoded novel protein SH2-B.

For both SH2-A and SH2-B, a cDNA library (the same one used above for the initial screening or any other library can be used) was screened by hybridization with fragments of the cDNA and the overlapping clones were isolated. The isolated clones were sequenced. The sequences were visually inspected for an in-frame ATG (start codon) and an in-frame stop codon 5' to the ATG. After the sequences were compared they were spliced together in the region of the overlap using UWGCG sequence analysis software. The eDNA clones of SH2-A and SH2-B were sequenced entirely on both DNA strands.

Figure 7A:
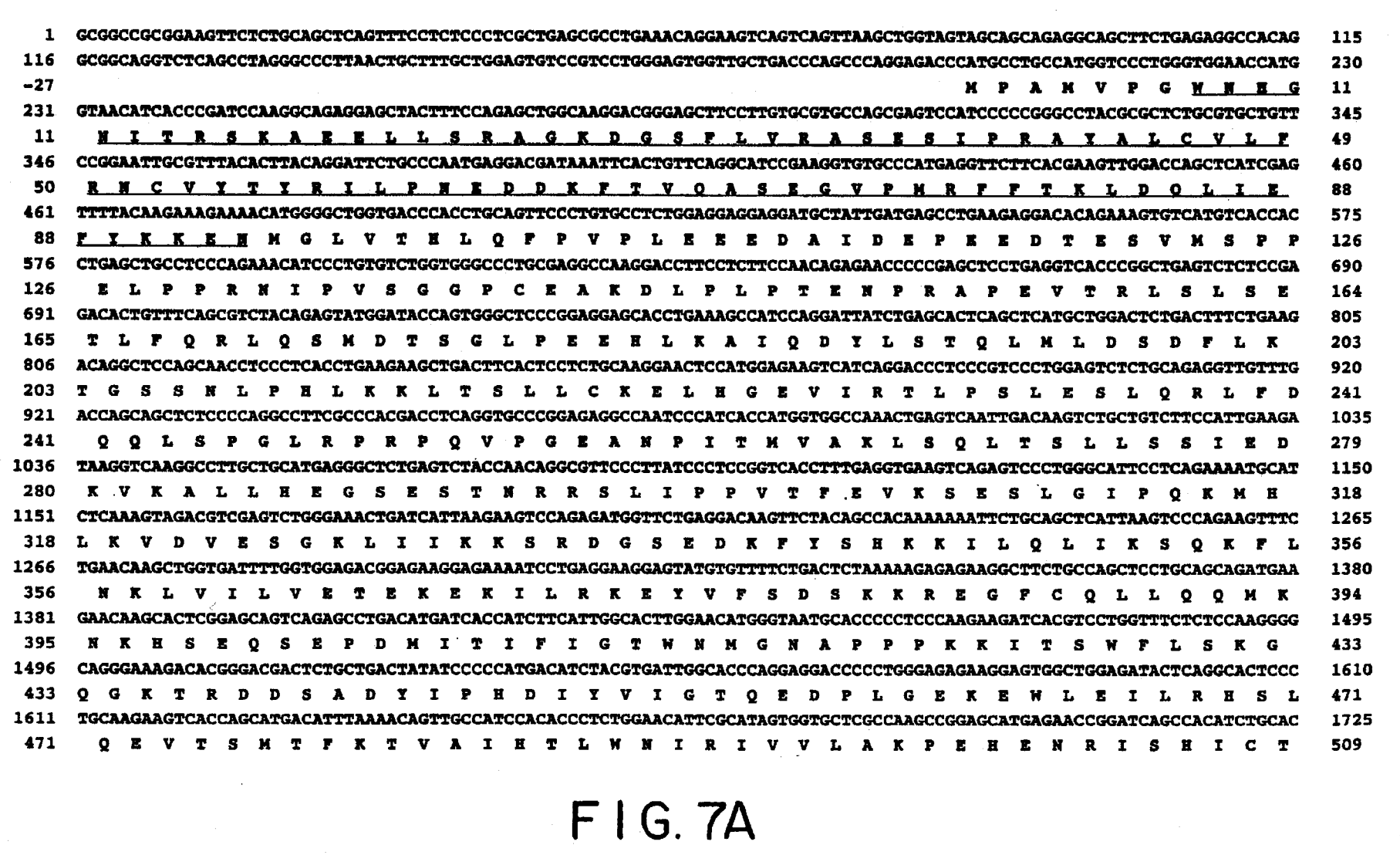
Figure 7B:
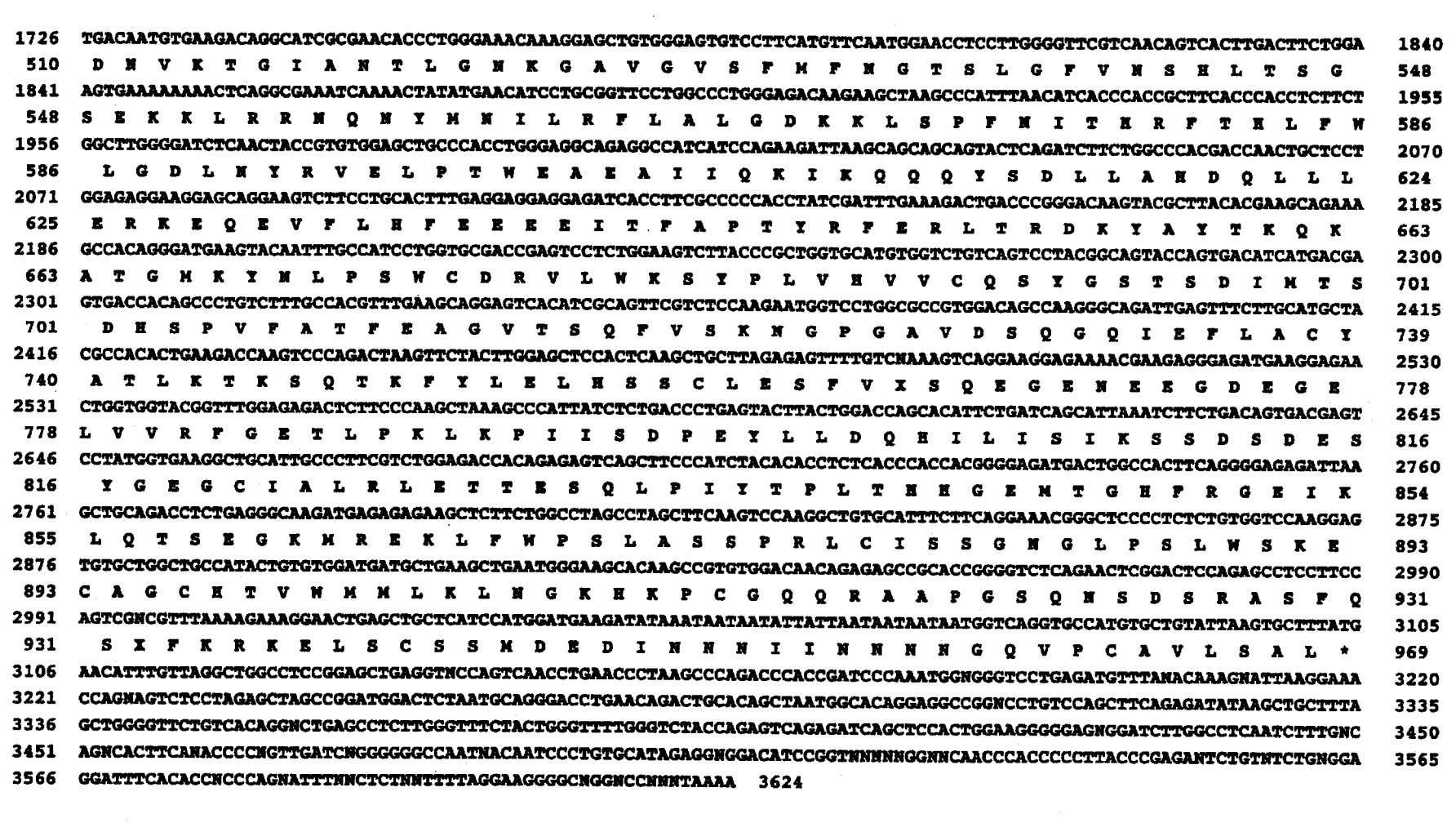
Figure 8A:
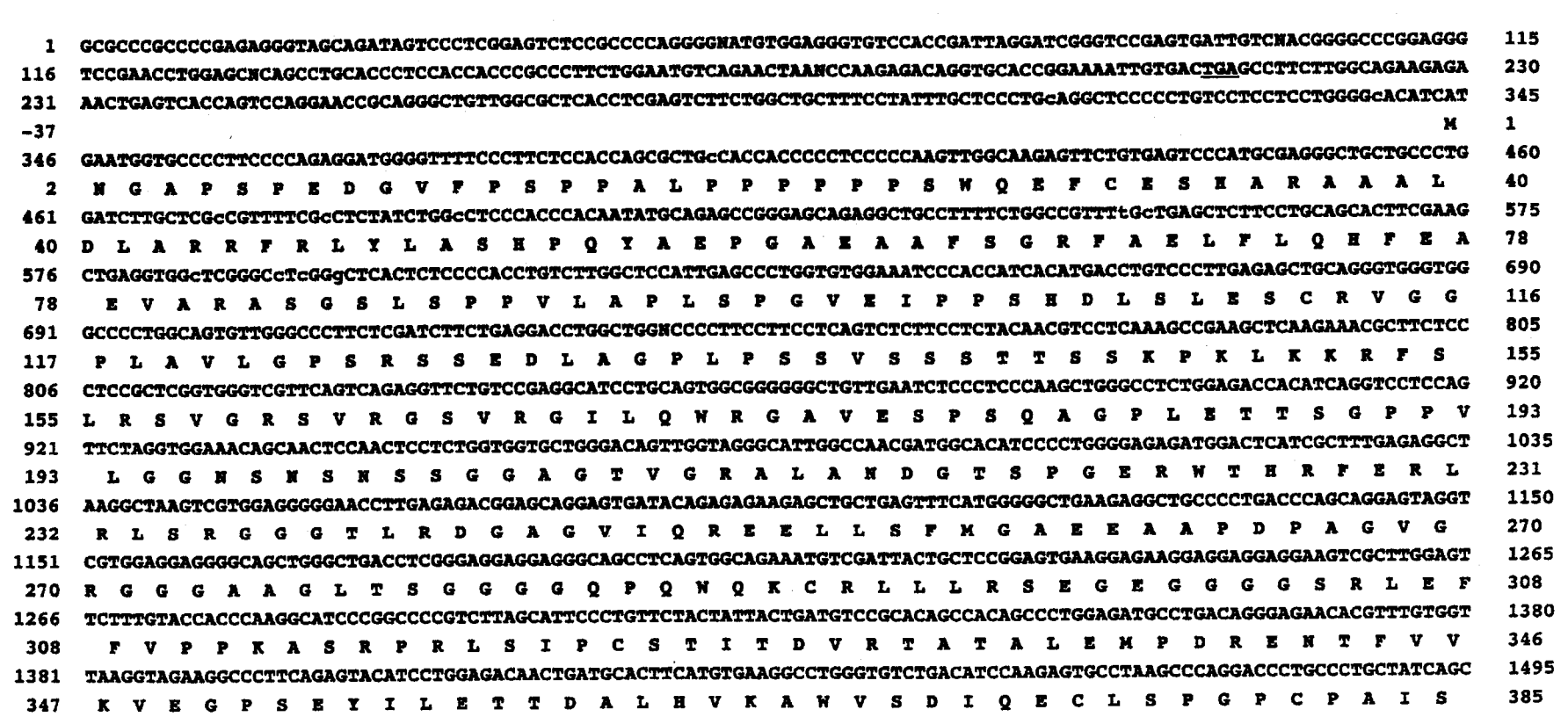
Figure 8B:
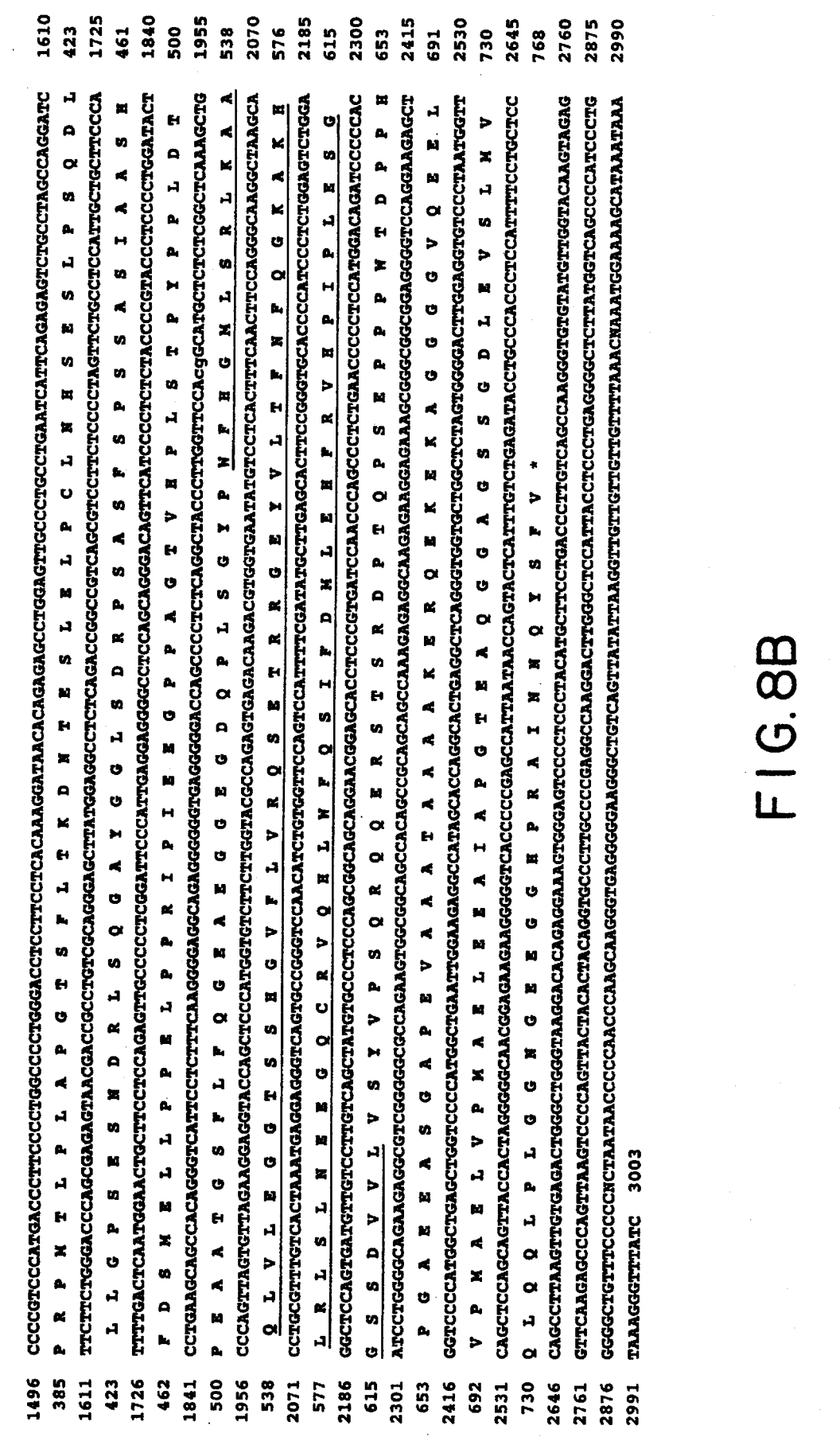

FIGS. 7 and 8 illustrate the sequences of the novel SH2-domain containing clones. FIG. 7 shows SH2-A (SEQ ID NO:13). The SH2 domain is underlined. The in-frame stop codon 5' to the ATG used as a putative start codon is underlined at nucleotide 103. FIG. 8 shows SH2-B (SEQ ID NO:14). The SH2 domain is underlined. The in-frame stop codon 5' to the ATG is underlined at nucleotide 209.

Mutagenesis of FceRIγCT

Since it had been demonstrated that the protein-protein interaction system was able to detect SH2 domain-dependent interactions, conservative mutagenesis of the tyrosine residues within the FceRIγCT was performed to the amino acid phenylalanine. These mutant LexA-FceRIγCT fusion proteins were used to test for interactions with various Vmw65 fusion proteins in yeast.

The tyrosine residues encoded by the FceRIγ CT cDNA were mutated to phenylalanine by two-step PCR mutagenesis. Two primers were used: 5'-ATG CTT CAG AGT TTC GAA AGT CTC CTG GTT CCT-3' (SEQ ID NO:7) and 5'-GGT GCT CAG GCC CGT GAA GAC ACC ATC TGA TTT-3'(SEQ ID NO:8), where the underlined region indicates the nucleotides changed. The first pair of PCR reactions used primers having SEQ ID NO:7 and SEQ ID NO:8 in separate PCR reactions with primer 5'-GGG ATC CTC ATG AAA GCG TTA ACG GCC AGG-3'(SEQ ID NO:9) which hybridizes to the LexA region of the plasmid. The reaction using SEQ ID NO:7 and SEQ ID NO:9 yielded product A. The reaction using SEQ ID NO:8 and SEQ ID NO:9 yielded product B. A second PCR reaction utilized the primer pair of 5'-GGC ATG CAG GCG GCC GCG AAT TCT CGA CTG AAG ATC CAA GTG CGA-3'(SEQ ID NO: 10) and 5'-CCG GAT CCT CGA AAT TAA CCC TCA CTA AAG GGA-Y(SEQ ID NO:11) which hybridize at the 5' end of the γ CT cDNA and in the T3 promoter region of the plasmid, respectively, and yielded product C. An aliquot of product A was combined with an aliquot of product C and the amplification repeated with the primer having SEQ ID NO:9 and the primer having SEQ ID NO:11. The same was done for an aliquot of product B combined with an aliquot of product C. These PCR products were purified (Wizard PCR preps, Promega), digested with EcoRI and SpeI, and each subcloned separately into p4108 cut with EcoRI and SpeI. The subclones were sequenced to verify the inclusion of the mutations. To obtain the double mutant, each of the 5' single mutant was used as a template and the procedure repeated with the primer having SEQ ID NO:10. Results of studies using the mutants are given in Tables 1 and 2 and are explained below.

The expression and activity of the PTKs Lck and Lyn were verified by immuno-blot analysis. FIG. 5 illustrates that the expression of the Lck and Lyn tyrosine kinases increases phosphotyrosine. Yeast transformants containing the LexA fusion indicated (top) and either Lck (A) or human Lyn (B) were grown in glucose (−) or galactose (+) and processed for immunoblotting with anti-phosphotyrosine antibody. The numbers on the left refer to the approximate molecular weights ($\times 10^3$) of the separated proteins.

Figures 5A, 5B:
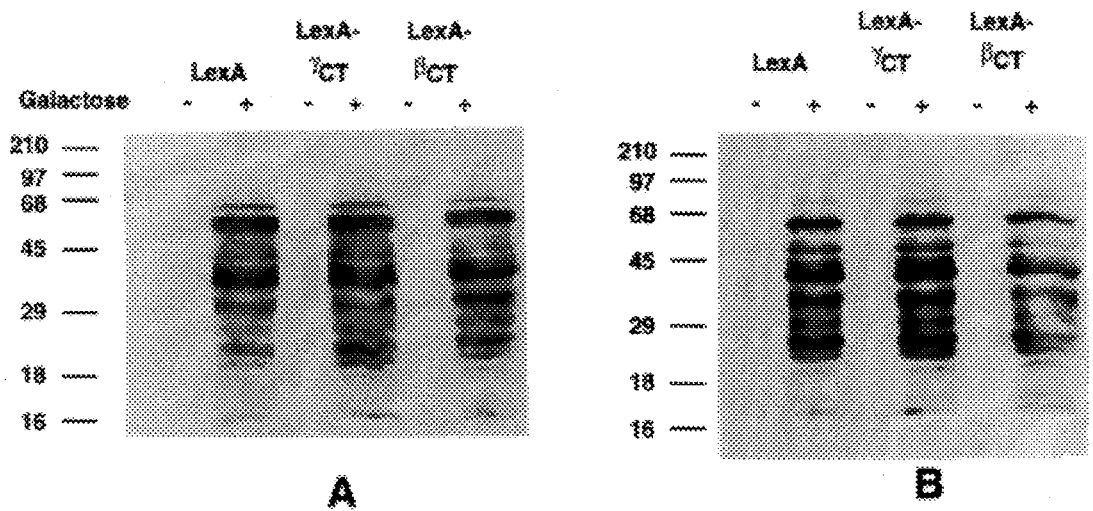
FIGS. 5A–5B shows the tight regulation of tyrosine phosphorylation in the host yeast cell by protein tyrosine kinases Lck and Lyn.

FIGS. 5A–5B demonstrate that both the full length Lck PTK, and the Lyn PTK were able to phosphorylate yeast proteins upon induction. Virtually no phosphotyrosine was detected in uninduced samples. Tyrosine phosphorylation in yeast was therefore dependent on the expression of heterologous PTKs.

Immunoprecipitation

To identify whether the LexA-FceRIγCT fusion protein was being phosphorylated on tyrosine, an immunoprecipitation was performed on cells containing either the fusion protein or the LexA protein alone. The immunoprecipitation was performed exactly as described in Franzusoff et al, Meth. Enz. 194, 662–682 (1991) using anti-LexA antibodies affinity purified as described (Koff et al, Science 257:1689 (1992)).

S-260 transformants containing various LexA-fusion proteins and with either p4140 (pGAL lck), p4141 (pGAL kin) or pRS415 were grown overnight in SC-Leu -Trp with 2% glucose. The cells were washed with sterile water and diluted 1:5 in the same media containing either 2% glucose or galactose. After 4–18 h, the $OD_{600}$ of the cells was determined and the samples were processed. 3 μg of affinity purified anti-LexA antiserum was bound to protein G sepharose (Pharmacia) and used to immunoprecipitate the fusion proteins. Extracts were pre-cleared with an unrelated IgG. Samples were boiled in 30 μl of Laemmli sample buffer and ½ was applied to a 12% polyacrylamide gel, transferred to nitrocellulose, and phosphotyrosine-containing proteins detected by antiphosphotyrosine monoclonal antibody (Upstate Biotechnology, Inc., Lake Placid, N.Y.).

Figure 6:
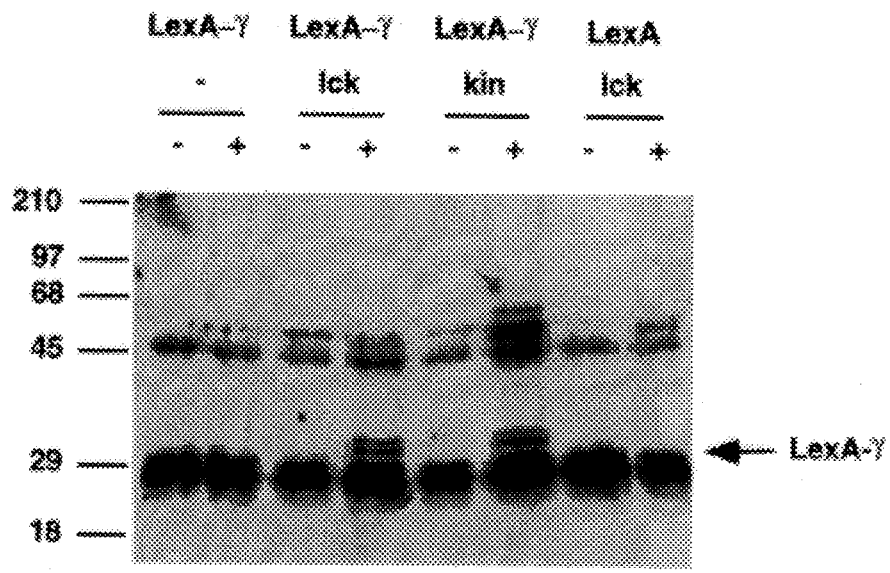
FIG. 6 shows the phosphorylation of the tyrosine containing protein LexA-FcεRIγCT by the protein tyrosine kinase Lck.

As shown in FIG. 6, a doublet of ~29 kD was observed only in those lanes where both LexA-γ and Lck are expressed. These observations confirm that Lck was capable of phosphorylating the FcεRIγ CT in yeast. Other ITAMs such as FcεRIβ and TcRζ are also phosphorylated in this system. The results demonstrate that LexA-FcεRIγCT is phosphorylated on tyrosine only when both Lck and LexA-FcεRIγCT are expressed in the same cell. The numbers on the left side of the figure refer to the approximate molecular weights ($\times 10^{-3}$) of the separated proteins.

The present method of detecting protein-protein interactions was shown to work using SH2 domains of proteins known by biochemical methods to interact with subunits of the FcεRI. Several candidate FcεRIγCT interacting proteins were cloned into p4064. The SH2 domains of human Syk (SykN=amino acids 11–111, SykC=amino acids 173–262, SykN+C=amino acids 11–262; Law et al, 1994, J. Biol. Chem. 269:12310–12319) were PCR amplified with primers to facilitate cloning into p4064 forming pVmw65-Syk SH2. The sequences of the resulting plasmids, pVmw65-SykN, pVmw65-SykN+C and pVmw65-SykC SH2 were confirmed and expression in yeast verified by immuno-blot analysis using anti-Syk and anti-Vmw65 antibodies. The human Lyn SH2 domain (Lyn=amino acids 124–229; Yamanashi et al., 1987. Mol. Cell. Biol. 7:237–243) was cloned into p4064 by PCR in a manner similar to the Syk SH2 domains, forming pVmw65-Lyn SH2. pVmw65-16 was a library plasmid selected at random for use as a control.

The results shown in Table I demonstrate that co-expression of all three components in yeast, Vmw65-Syk N+C SH2, the LexA-FcεRIγ CT, and Lck, results in the production of β-galactosidase (β-gal). Removal of any one of the components results in the complete loss of β-gal activity.

TABLE 1

|  | Syk N + C SH2 | Syk N − SH2 | Syk C − SH2 | Lyn SH2 |
| --- | --- | --- | --- | --- |
| gamma | 559 | 0 | 0 | 0 |
| gamma F64 | 0 | 0 | 0 | 0 |
| gamma F75 | 0 | 0 | 0 | 0 |
| gamma FF | 0 | 0 | 0 | 0 |
| beta | 1070 | 0 | 593 | 858 |

Numbers are β-Galactosidase units

The interactions of the different Syk SH2 domains with either of two different ITAMs, FcεRIγCT and FcεRIβCT were also studied and the results are summarized in Table I.

As shown in Table I, mutation of either of the FcεRIγ CT tyrosine residues within the ITAM (Tyr64 and Tyr75) eliminated the strong interaction with the tandem Syk SH2 protein. The individual Syk SH2 domains did not interact with FcεRIγ, CT, although the C-terminal SH2 interacted strongly with the FcεRIβ CT. The Lyn SH2 domain interacted with the FcεRIβCT but not the FcεRIγCT. These interactions were different than with FcεRIγCT, since the C-terminal SH2 domain of Syk interacted strongly with FcεRIβCT but not FcεRIγCT. The fact that the interaction of FcεRIβCT occurs with the SykC SH2 and Lyn SH2 domains demonstrated the specificity of ITAM-SH2 domain interactions as FcεRIγCT interacts with neither. These results demonstrated the specificity of the SH2 interactions in the claimed method system.

To determine if the SH2 domains were required for interaction with LexA-γCT, deletions were constructed and tested for β-galactosidase activity in the assay. Deletions of SH2-A (SH2A Δ) and SH2-B (SH2B Δ) were generated by PCR and subcloned into p4064 at the Eco RI and XbaI sites. Expression of the fusion proteins was confirmed by immunoblotting with 9E10 monoclonal antibody or anti-Vmw65 antiserum. Only those deletions containing the SH2 domain were still able to interact with LexA-γCT. See Table 2 below.

TABLE 2

|  | SH2 − A | SH2 − A Δ | SH2 − B | SH2 − B Δ |
| --- | --- | --- | --- | --- |
| gamma | 21 | 0 | 1255 | 0 |
| gamma F64 | 32 | 0 | 157 | 0 |
| gamma F75 | 0 | 0 | 0 | 0 |
| gamma FF | 0 | 0 | 0 | 0 |
| beta | 960 | 0 | 1080 | 0 |

These results indicate that the SH2 domains are essential to allow for the interaction to take place. These results also indicate that the SH2 domains are interacting specifically with the phosphotyrosine containing proteins (ITAMS). The SH2 domains are required components of the fusion proteins in order to facilitate interaction with LexA-ITAMs.

The interaction between LexA-TCT and SH2-A and SH2-B is also dependent on the presence of tyrosine residues within the γCT portion of the fusion. Site-directed mutagenesis of both tyrosines independently and together reveals that the N-terminal Tyr64 can be mutated to phenylalanine with no detectable loss of interaction (Table 2), while mutation of the C-terminal Tyr75 results in the abolition of all interactions. These results are in contrast to the observation with the Syk SH2 domains (Table 1), where both tyrosine residues of the ITAM were required for an interaction to be detected.

Other changes and modifications to the above described method that do not materially change the spirit of the invention will be apparent to those skilled in the art and are included within the scope of the present invention.

We claim:

1. A method for detecting an interaction between a first test protein and a second test protein, comprising:
   (A) introducing a first chimeric gene, a second chimeric gene and a third gene into a *Saccharomyces cerevisiae* or mammalian host cell containing a detectable gene which expresses a detectable protein when the detectable gene is transcribed, wherein;
      (i) said first chimeric gene encodes a first hybrid protein, said first hybrid protein comprising:
         (a) a DNA-binding domain that recognizes a binding site on the detectable gene in the host cell; and
         (b) a first test protein or fragment thereof to be tested for interaction with a second test protein or fragment thereof, wherein the interact loft of said first and second test proteins requires a post-translational interaction of said first test protein with a third test protein;
      (ii) said second chimeric gene encodes a second hybrid protein, said second hybrid protein comprising:
         (a) a transcriptional activation moiety; and
         (b) a second test protein or fragment thereof to be tested for interaction with said first test protein or fragment thereof; and
      (iii) said third gene comprising a DNA sequence that encodes a third test protein or fragment thereof to be tested for interaction with said first test protein;
   wherein said first chimeric gene, second chimeric gene and third gene also contain an inducible promoter region such that expression of said genes in the host cell is regulated;
   (B) subjecting the host cell to conditions such that said first hybrid protein, said second hybrid protein and said third test protein are expressed in sufficient quantity for said third test protein to interact with said first test protein thereby enabling the interaction between said first test protein and said second test protein, and the formation of a complex of the DNA binding moiety of said first hybrid protein and the transcriptional activation moiety of said second hybrid protein which in turn results in the activation and transcription of the detectable gene; and
   (C) determining whether the detectable gene has been transcribed, the transcription of the detectable gene being indicative of whether an interaction has occurred between said first and second test proteins.

2. The method of claim 1, wherein the DNA binding moiety and the transcriptional activation moiety are derived from a single transcriptional activator.

3. The method of claim 1, wherein the DNA binding moiety and the transcriptional activation moiety are derived from different proteins.

4. The method of claim 1, wherein said detectable protein is selected from the group consisting of β-galactosidase, green fluorescent protein luciferase, alkaline phosphatase and chloramphenical acetyl transferase.

5. The method of claim 1, wherein the detectable gene expresses a selectable marker comprising a protein involved in nutrient biosynthesis.

6. The method of claim 1, wherein the inducible promoter is a galactose inducible promoter.

7. A method for detecting an interaction between a first test protein and a second test protein, said interaction dependent upon the post-translational modification of the first test protein by a third test protein, comprising:
   (A) introducing into a *Saccharomyces cerevisiae* or mammalian host cell containing a detectable gene which expresses a detectable protein when the detectable gene is transcribed, the following:
      (i) a first chimeric gene encoding a first hybrid protein, said hybrid protein comprising:

(a) a DNA-binding moiety that recognizes a binding site on the detectable gene in the host cell; and (b) a first test protein or fragment thereof to be tested for interaction with a second test protein or fragment thereof, wherein the interaction of said first and second test proteins requires a post-translational modification of said first test protein by a third test protein;

(ii) a second chimeric gene comprising a DNA sequence that encodes a second hybrid protein, said second hybrid protein comprising:

(a) a transcriptional activation moiety; and (b) a second test protein or fragment thereof to be tested for interaction with said first test protein or fragment thereof; and (iii) a third gene comprising a DNA sequence that encodes a third test protein or fragment thereof which post-translationally modifies said first test protein;

wherein said first chimeric gene, second chimeric gene and third gene also contain an inducible promoter region such that expression of said genes in the host cell is regulated;

(B) subjecting the host cell to conditions such that said first hybrid protein, said second hybrid protein and said third test protein are expressed in sufficient quantity for said third test protein to post-translationally modify said first test protein thereby enabling the formation of a complex between said first test protein and said second test protein, and the formation of a complex of the DNA binding moiety of said first hybrid protein and the transcriptional activation moiety of said second hybrid protein which in turn results in the activation and transcription of the detectable gene; and (C) determining whether the detectable gene has been transcribed, the transcription of the detectable gene being indicative of whether an interaction has occurred between said first and second test proteins.

8. The method of claim 7, wherein said third test protein is a protein kinase.

9. The method of claim 7, wherein said first test protein comprises a subunit of a protein containing an immunoreceptor tyrosine-based activation motif (ITAM).

10. The method of claim 7, wherein said second test protein is a src-homology 2 (SH2) containing protein.

11. The method of claim 8, wherein said third protein is a tyrosine kinase.

12. The method of claim 9, wherein said first test protein is selected from the group consisting of high affinity IgE receptor FcεRIγ and FcεRIβ subunits and T cell receptor ζ chain.

13. The method of claim 10, wherein said second test protein is selected from the group consisting of Syk and Lyn.

14. The method of claim 11, wherein said third test protein is selected from the group consisting of Lck and Lyn.

15. The method of claim 7, wherein a) the host cell is *Saccharomyces cerevisiae;* b) the host cell contains a detectable gene expressing β-galactosidase;

c) said first hybrid protein comprises *E.coli* LexA fused to FcεRIγCT;

d) said second hybrid protein comprises HSV1Vmw65 fused to the SH2 domains of Syk;

e) said third test protein is Lck; and f) the inducible promoter region is inducible by galactose.

16. A cDNA consisting of SEQ ID NO:13.

17. A cDNA consisting of SEQ ID NO:15 .

18. A protein SH2-A consisting of amino acid science SEQ ID NO:14.

19. A protein SH2-B consisting of acid SEQ ID NO:16.

20. A kit for the detection in a *Saccharomyces cerevisiae* or mammalian host cell of interactions between test proteins wherein said interaction is dependent upon post-translational modification of a first test protein by a third test protein, comprising three or more DNA sequences comprising a first plasmid encoding a first hybrid protein, said first hybrid protein comprising a DNA-binding moiety fused to a first protein of interest, said first protein to be tested for interaction with a second test protein wherein said first test protein must be post translationally modified by the third test protein for it to interact with said second test protein;

b) a second plasmid encoding a second hybrid protein, said second hybrid protein comprising a transcriptional activation moiety fused to cloning sites for a cDNA library or specific fusion proteins to be tested for interaction with said first test protein;

c) a third plasmid encoding a third test protein having protein modification activity for said first test protein; and d) a DNA comprising a reporter construct.

* * * * *

UNITED STATES PATENT AND TRADEMARK OFFICE
CERTIFICATE OF CORRECTION

PATENT NO. : 5,637,463
DATED : June 10, 1997
INVENTOR(S) : Stephen Dalton, Jarema Peter Kochan, Mark Andrew Osborne It is certified that error appears in the above-indentified patent and that said Letters Patent is hereby corrected as shown below:

In claim 1, line 47, delete "interact loft" and insert -- interaction --.

In claim 12, line 3, delete "FceRIγ" and insert -- FcεRIγ --.

In claim 18, line 21, delete "science" and insert -- sequence --.

In claim 19, line 23, before the word "acid" insert -- amino --.

In claim 20, line 30, insert -- a) -- at the beginning of line before "a first plasmid".

Signed and Sealed this

Second Day of December, 1997

BRUCE LEHMAN

*Attest:*

*Attesting Officer*    Commissioner of Patents and Trademarks

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 45 base pairs
( B ) TYPE: nucleic acid
( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GGCATCCAGG CGGCCGCGAA TTCTCGACTG AAGATCCAAG TGCGA 45

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

GGCACTAGTC TACTGTGGTG GTTTCTC 27

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GGCCGCGCCA AAGAAGAAGA GAAAGGTAGC G 31

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

AATTCGCTAC CTTTCTCTTC TTCTTTGGCG C 31

( 2 ) INFORMATION FOR SEQ ID NO:5:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA (genomic)

(iii) HYPOTHETICAL: NO (iv) ANTI-SENSE: NO (xi) SEQUENCE DESCRIPTION: SEQ ID NO:5:

GATCCCCAAA GAAGAAGAGA AAGGTAGAGC AGAAGCTGAT TAGCGAGGAA GATCTGAATG    60

CG    62

(2) INFORMATION FOR SEQ ID NO:6:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

TCGACGCATT CAGATCTTCC TCGCTAATCA GCTTCTGCTC TACCTTTCTC TTCTTCTTTG    60

GG    62

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

ATGCTTCAGA GTTTCGAAAG TCTCCTGGTT CCT    33

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

GGTGCTCAGG CCCGTGAAGA CACCATCTGA TTT    33

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GGGATCCTCA TGAAAGCGTT AACGGCCAGG                                30

( 2 ) INFORMATION FOR SEQ ID NO:10:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

GGCATGCAGG CGGCCGCGAA TTCTCGACTG AAGATCCAAG TGCGA               45

( 2 ) INFORMATION FOR SEQ ID NO:11:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

CCGGATCCTC GAAATTAACC CTCACTAAAG GGA                            33

( 2 ) INFORMATION FOR SEQ ID NO:12:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

CTTTAGTGCA CA                                                   12

( 2 ) INFORMATION FOR SEQ ID NO:13:

( i ) SEQUENCE CHARACTERISTICS:
      ( A ) LENGTH: 3624 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: YES ( i v ) ANTI-SENSE: NO ( x i ) SEQUENCE DESCRIPTION: SEQ ID NO:13:

```
GCGGCCGCGG AAGTTCTCTG CAGCTCAGTT TCCTCTCCCT CGCTGAGCGC CTGAAACAGG    60
AAGTCAGTCA GTTAAGCTGG TAGTAGCAGC AGAGGCAGCT TCTGAGAGGC CACAGGCGGC   120
AGGTCTCAGC CTAGGGCCCT TAACTGCTTT GCTGGAGTGT CCGTCCTGGG AGTGGTTGCT   180
GACCCAGCCC AGGAGACCCA TGCCTGCCAT GGTCCCTGGG TGGAACCATG GTAACATCAC   240
CCGATCCAAG GCAGAGGAGC TACTTCCAG AGCTGGCAAG GACGGGAGCT TCCTTGTGCG    300
TGCCAGCGAG TCCATCCCCC GGGCCTACGC GCTCTGCGTG CTGTTCCGGA ATTGCGTTTA   360
CACTTACAGG ATTCTGCCCA ATGAGGACGA TAAATTCACT GTTCAGGCAT CCGAAGGTGT   420
GCCCATGAGG TTCTTCACGA AGTTGGACCA GCTCATCGAG TTTTACAAGA AAGAAAACAT   480
GGGGCTGGTG ACCCACCTGC AGTTCCCTGT GCCTCTGGAG GAGGAGGATG CTATTGATGA   540
GCCTGAAGAG GACACAGAAA GTGTCATGTC ACCACCTGAG CTGCCTCCCA GAAACATCCC   600
TGTGTCTGGT GGGCCCTGCG AGGCCAAGGA CCTTCCTCTT CCAACAGAGA ACCCCCGAGC   660
TCCTGAGGTC ACCCGGCTGA GTCTCTCCGA GACACTGTTT CAGCGTCTAC AGAGTATGGA   720
TACCAGTGGG CTCCCGGAGG AGCACCTGAA AGCCATCCAG GATTATCTGA GCACTCAGCT   780
CATGCTGGAC TCTGACTTTC TGAAGACAGG CTCCAGCAAC CTCCCTCACC TGAAGAAGCT   840
GACTTCACTC CTCTGCAAGG AACTCCATGG AGAAGTCATC AGGACCCTCC CGTCCCTGGA   900
GTCTCTGCAG AGGTTGTTTG ACCAGCAGCT CTCCCCAGGC CTTCGCCCAC GACCTCAGGT   960
GCCCGGAGAG GCCAATCCCA TCACCATGGT GGCCAAACTG AGTCAATTGA CAAGTCTGCT  1020
GTCTTCCATT GAAGATAAGG TCAAGGCCTT GCTGCATGAG GGCTCTGAGT CTACCAACAG  1080
GCGTTCCCTT ATCCCTCCGG TCACCTTTGA GGTGAAGTCA GAGTCCCTGG CATTCCTCA   1140
GAAAATGCAT CTCAAAGTAG ACGTCGAGTC TGGGAAACTG ATCATTAAGA AGTCCAGAGA  1200
TGGTTCTGAG GACAAGTTCT ACAGCCACAA AAAAATTCTG CAGCTCATTA AGTCCCAGAA  1260
GTTTCTGAAC AAGCTGGTGA TTTTGGTGGA GACGGAGAAG GAGAAAATCC TGAGGAAGGA  1320
GTATGTGTTT TCTGACTCTA AAAGAGAGA AGGCTTCTGC CAGCTCCTGC AGCAGATGAA   1380
GAACAAGCAC TCGGAGCAGT CAGAGCCTGA CATGATCACC ATCTTCATTG GCACTTGGAA  1440
CATGGGTAAT GCACCCCCTC CCAAGAAGAT CACGTCCTGG TTTCTCTCCA AGGGGCAGGG  1500
AAAGACACGG GACGACTCTG CTGACTATAT CCCCCATGAC ATCTACGTGA TTGGCACCCA  1560
GGAGGACCCC CTGGGAGAGA AGGAGTGGCT GGAGATACTC AGGCACTCCC TGCAAGAAGT  1620
CACCAGCATG ACATTTAAAA CAGTTGCCAT CCACACCCTC TGGAACATTC GCATAGTGGT  1680
GCTCGCCAAG CCGGAGCATG AGAACCGGAT CAGCCACATC TGCACTGACA ATGTGAAGAC  1740
AGGCATCGCG AACACCCTGG GAAACAAAGG AGCTGTGGGA GTGTCCTTCA TGTTCAATGG  1800
AACCTCCTTG GGGTTCGTCA ACAGTCACTT GACTTCTGGA AGTGAAAAAA AACTCAGGCG  1860
AAATCAAAAC TATATGAACA TCCTGCGGTT CCTGGCCCTG GGAGACAAGA AGCTAAGCCC  1920
ATTAACATC ACCCACCGCT TCACCCACCT CTTCTGGCTT GGGGATCTCA ACTACCGTGT  1980
GGAGCTGCCC ACCTGGGAGG CAGAGGCCAT CATCCAGAAG ATTAAGCAGC AGCAGTACTC  2040
AGATCTTCTG GCCCACGACC AACTGCTCCT GGAGAGGAAG GAGCAGGAAG TCTTCCTGCA  2100
CTTTGAGGAG GAGGAGATCA CCTTCGCCCC CACCTATCGA TTTGAAAGAC TGACCCGGGA  2160
CAAGTACGCT TACACGAAGC AGAAAGCCAC AGGGATGAAG TACAATTTGC CATCCTGGTG  2220
CGACCGAGTC CTCTGGAAGT CTTACCCGCT GGTGCATGTG GTCTGTCAGT CCTACGGCAG  2280
TACCAGTGAC ATCATGACGA GTGACCACAG CCCTGTCTTT GCCACGTTTG AAGCAGGAGT  2340
```

-continued

```
CACATCGCAG TTCGTCTCCA AGAATGGTCC TGGCGCCGTG GACAGCCAAG GGCAGATTGA    2400
GTTTCTTGCA TGCTACGCCA CACTGAAGAC CAAGTCCCAG ACTAAGTTCT ACTTGGAGCT    2460
CCACTCAAGC TGCTTAGAGA GTTTTGTCNA AAGTCAGGAA GGAGAAAACG AAGAGGGAGA    2520
TGAAGGAGAA CTGGTGGTAC GGTTTGGAGA GACTCTTCCC AAGCTAAAGC CCATTATCTC    2580
TGACCCTGAG TACTTACTGG ACCAGCACAT TCTGATCAGC ATTAAATCTT CTGACAGTGA    2640
CGAGTCCTAT GGTGAAGGCT GCATTGCCCT TCGTCTGGAG ACCACAGAGA GTCAGCTTCC    2700
CATCTACACA CCTCTCACCC ACCACGGGGA GATGACTGGC CACTTCAGGG GAGAGATTAA    2760
GCTGCAGACC TCTGAGGGCA AGATGAGAGA GAAGCTCTTC TGGCCTAGCC TAGCTTCAAG    2820
TCCAAGGCTG TGCATTTCTT CAGGAAACGG GCTCCCCTCT CTGTGGTCCA AGGAGTGTGC    2880
TGGCTGCCAT ACTGTGTGGA TGATGCTGAA GCTGAATGGG AAGCACAAGC CGTGTGGACA    2940
ACAGAGAGCC GCACCGGGGT CTCAGAACTC GGACTCCAGA GCCTCCTTCC AGTCGNCGTT    3000
TAAAAGAAAG GAACTGAGCT GCTCATCCAT GGATGAAGAT ATAAATAATA ATATTATTAA    3060
TAATAATAAT GGTCAGGTGC CATGTGCTGT ATTAAGTGCT TTATGAACAT TTGTTAGGCT    3120
GGCCTCCGGA GCTGAGGTNC CAGTCAACCT GAACCCTAAG CCCAGACCCA CCGATCCCAA    3180
ATGGNGGGTC CTGAGATGTT TANACAAAGN ATTAAGGAAA CCAGNAGTCT CCTAGAGCTA    3240
GCCGGATGGA CTCTAATGCA GGGACCTGAA CAGACTGCAC AGCTAATGGC ACAGGAGGCC    3300
GGNCCTGTCC AGCTTCAGAG ATATAAGCTG CTTTAGCTGG GGTTCTGTCA CAGGNCTGAG    3360
CCTCTTGGGT TTCTACTGGG TTTTGGGTCT ACCAGAGTCA GAGATCAGCT CCACTGGAAG    3420
GGGGAGNGGA TCTTGGCCTC AATCTTTGNC AGNCACTTCA NACCCCNGTT GATCNGGGGG    3480
GCCAATNACA ATCCCTGTGC ATAGAGGNGG ACATCCGGTN NNNNGGNNCA ACCCACCCCC    3540
TTACCCGAGA NTCTGTNTCT GNGGAGGATT TCACACCNCC CAGNATTTNN CTCTNNTTTT    3600
AGGAAGGGGC NGGNCCNNNT AAAA                                          3624
```

( 2 ) INFORMATION FOR SEQ ID NO:14:

( i ) SEQUENCE CHARACTERISTICS:
        ( A ) LENGTH: 968 amino acids
        ( B ) TYPE: amino acid
        ( C ) STRANDEDNESS: Not Relevant
        ( D ) TOPOLOGY: Not Relevant ( i i ) MOLECULE TYPE: protein ( x i ) SEQUENCE DESCRIPTION: SEQ ID NO:14:

```
Met Pro Ala Met Val Pro Gly Trp Asn His Gly Asn Ile Thr Arg Ser
 1               5                  10                  15

Lys Ala Glu Glu Leu Leu Ser Arg Ala Gly Lys Asp Gly Ser Phe Leu
            20                  25                  30

Val Arg Ala Ser Glu Ser Ile Pro Arg Ala Tyr Ala Leu Cys Val Leu
        35                  40                  45

Phe Arg Asn Cys Val Tyr Thr Tyr Arg Ile Leu Pro Asn Glu Asp Asp
    50                  55                  60

Lys Phe Thr Val Gln Ala Ser Glu Gly Val Pro Met Arg Phe Phe Thr
65                  70                  75                  80

Lys Leu Asp Gln Leu Ile Glu Phe Tyr Lys Lys Glu Asn Met Gly Leu
                85                  90                  95

Val Thr His Leu Gln Phe Pro Val Pro Leu Glu Glu Glu Asp Ala Ile
            100                 105                 110

Asp Glu Pro Glu Glu Asp Thr Glu Ser Val Met Ser Pro Pro Glu Leu
        115                 120                 125
```

```
Pro  Pro  Arg  Asn  Ile  Pro  Val  Ser  Gly  Gly  Pro  Cys  Glu  Ala  Lys  Asp
     130                 135                 140

Leu  Pro  Leu  Pro  Thr  Glu  Asn  Pro  Arg  Ala  Pro  Glu  Val  Thr  Arg  Leu
145                      150                 155                           160

Ser  Leu  Ser  Glu  Thr  Leu  Phe  Gln  Arg  Gln  Ser  Met  Asp  Thr  Ser
               165                      170                      175

Gly  Leu  Pro  Glu  Glu  His  Leu  Lys  Ala  Ile  Gln  Asp  Tyr  Leu  Ser  Thr
               180                 185                           190

Gln  Leu  Met  Leu  Asp  Ser  Asp  Phe  Leu  Lys  Thr  Gly  Ser  Ser  Asn  Leu
          195                 200                      205

Pro  His  Leu  Lys  Lys  Leu  Thr  Ser  Leu  Leu  Cys  Lys  Glu  Leu  His  Gly
     210                      215                 220

Glu  Val  Ile  Arg  Thr  Leu  Pro  Ser  Leu  Glu  Ser  Leu  Gln  Arg  Leu  Phe
225                      230                 235                           240

Asp  Gln  Gln  Leu  Ser  Pro  Gly  Leu  Arg  Pro  Arg  Pro  Gln  Val  Pro  Gly
               245                      250                      255

Glu  Ala  Asn  Pro  Ile  Thr  Met  Val  Ala  Lys  Leu  Ser  Gln  Leu  Thr  Ser
               260                 265                           270

Leu  Leu  Ser  Ser  Ile  Glu  Asp  Lys  Val  Lys  Ala  Leu  Leu  His  Glu  Gly
          275                      280                      285

Ser  Glu  Ser  Thr  Asn  Arg  Arg  Ser  Leu  Ile  Pro  Pro  Val  Thr  Phe  Glu
290                           295                 300

Val  Lys  Ser  Glu  Ser  Leu  Gly  Ile  Pro  Gln  Lys  Met  His  Leu  Lys  Val
305                      310                 315                           320

Asp  Val  Glu  Ser  Gly  Lys  Leu  Ile  Ile  Lys  Lys  Ser  Arg  Asp  Gly  Ser
                    325                      330                      335

Glu  Asp  Lys  Phe  Tyr  Ser  His  Lys  Lys  Ile  Leu  Gln  Leu  Ile  Lys  Ser
               340                      345                      350

Gln  Lys  Phe  Leu  Asn  Lys  Leu  Val  Ile  Leu  Val  Glu  Thr  Glu  Lys  Glu
          355                      360                      365

Lys  Ile  Leu  Arg  Lys  Glu  Tyr  Val  Phe  Ser  Asp  Ser  Lys  Lys  Arg  Glu
     370                      375                 380

Gly  Phe  Cys  Gln  Leu  Leu  Gln  Gln  Met  Lys  Asn  Lys  His  Ser  Glu  Gln
385                      390                 395                           400

Ser  Glu  Pro  Asp  Met  Ile  Thr  Ile  Phe  Ile  Gly  Thr  Trp  Asn  Met  Gly
                    405                      410                      415

Asn  Ala  Pro  Pro  Pro  Lys  Lys  Ile  Thr  Ser  Trp  Phe  Leu  Ser  Lys  Gly
               420                      425                      430

Gln  Gly  Lys  Thr  Arg  Asp  Asp  Ser  Ala  Asp  Tyr  Ile  Pro  His  Asp  Ile
          435                      440                      445

Tyr  Val  Ile  Gly  Thr  Gln  Glu  Asp  Pro  Leu  Gly  Glu  Lys  Glu  Trp  Leu
450                           455                 460

Glu  Ile  Leu  Arg  His  Ser  Leu  Gln  Glu  Val  Thr  Ser  Met  Thr  Phe  Lys
465                      470                 475                           480

Thr  Val  Ala  Ile  His  Thr  Leu  Trp  Asn  Ile  Arg  Ile  Val  Val  Leu  Ala
               485                      490                           495

Lys  Pro  Glu  His  Glu  Asn  Arg  Ile  Ser  His  Ile  Cys  Thr  Asp  Asn  Val
               500                      505                      510

Lys  Thr  Gly  Ile  Ala  Asn  Thr  Leu  Gly  Asn  Lys  Gly  Ala  Val  Gly  Val
               515                      520                      525

Ser  Phe  Met  Phe  Asn  Gly  Thr  Ser  Leu  Gly  Phe  Val  Asn  Ser  His  Leu
     530                      535                 540

Thr  Ser  Gly  Ser  Glu  Lys  Lys  Leu  Arg  Arg  Asn  Gln  Asn  Tyr  Met  Asn
```

-continued

```
 545                            550                           555                           560

Ile  Leu  Arg  Phe  Leu  Ala  Leu  Gly  Asp  Lys  Lys  Leu  Ser  Pro  Phe  Asn
                         565                      570                      575

Ile  Thr  His  Arg  Phe  Thr  His  Leu  Phe  Trp  Leu  Gly  Asp  Leu  Asn  Tyr
                         580                      585                      590

Arg  Val  Glu  Leu  Pro  Thr  Trp  Glu  Ala  Glu  Ala  Ile  Ile  Gln  Lys  Ile
               595                      600                      605

Lys  Gln  Gln  Gln  Tyr  Ser  Asp  Leu  Leu  Ala  His  Asp  Gln  Leu  Leu  Leu
          610                      615                      620

Glu  Arg  Lys  Glu  Gln  Glu  Val  Phe  Leu  His  Phe  Glu  Glu  Glu  Glu  Ile
     625                      630                      635                           640

Thr  Phe  Ala  Pro  Thr  Tyr  Arg  Phe  Glu  Arg  Leu  Thr  Arg  Asp  Lys  Tyr
                         645                      650                           655

Ala  Tyr  Thr  Lys  Gln  Lys  Ala  Thr  Gly  Met  Lys  Tyr  Asn  Leu  Pro  Ser
                    660                      665                      670

Trp  Cys  Asp  Arg  Val  Leu  Trp  Lys  Ser  Tyr  Pro  Leu  Val  His  Val  Val
                         675                      680                      685

Cys  Gln  Ser  Tyr  Gly  Ser  Thr  Ser  Asp  Ile  Met  Thr  Ser  Asp  His  Ser
          690                      695                      700

Pro  Val  Phe  Ala  Thr  Phe  Glu  Ala  Gly  Val  Thr  Ser  Gln  Phe  Val  Ser
     705                      710                      715                           720

Lys  Asn  Gly  Pro  Gly  Ala  Val  Asp  Ser  Gln  Gly  Gln  Ile  Glu  Phe  Leu
                         725                      730                      735

Ala  Cys  Tyr  Ala  Thr  Leu  Lys  Thr  Lys  Ser  Gln  Thr  Lys  Phe  Tyr  Leu
                    740                      745                      750

Glu  Leu  His  Ser  Ser  Cys  Leu  Glu  Ser  Phe  Val  Xaa  Ser  Gln  Glu  Gly
               755                      760                      765

Glu  Asn  Glu  Glu  Gly  Asp  Glu  Gly  Glu  Leu  Val  Val  Arg  Phe  Gly  Glu
          770                      775                      780

Thr  Leu  Pro  Lys  Leu  Lys  Pro  Ile  Ile  Ser  Asp  Pro  Glu  Tyr  Leu  Leu
     785                      790                      795                           800

Asp  Gln  His  Ile  Leu  Ile  Ser  Ile  Lys  Ser  Ser  Asp  Ser  Asp  Glu  Ser
                         805                      810                           815

Tyr  Gly  Glu  Gly  Cys  Ile  Ala  Leu  Arg  Leu  Glu  Thr  Thr  Glu  Ser  Gln
                    820                      825                      830

Leu  Pro  Ile  Tyr  Thr  Pro  Leu  Thr  His  His  Gly  Glu  Met  Thr  Gly  His
               835                      840                      845

Phe  Arg  Gly  Glu  Ile  Lys  Leu  Gln  Thr  Ser  Glu  Gly  Lys  Met  Arg  Glu
          850                      855                      860

Lys  Leu  Phe  Trp  Pro  Ser  Leu  Ala  Ser  Ser  Pro  Arg  Leu  Cys  Ile  Ser
     865                      870                      875                           880

Ser  Gly  Asn  Gly  Leu  Pro  Ser  Leu  Trp  Ser  Lys  Glu  Cys  Ala  Gly  Cys
                         885                      890                           895

His  Thr  Val  Trp  Met  Met  Leu  Lys  Leu  Asn  Gly  Lys  His  Lys  Pro  Cys
                    900                      905                      910

Gly  Gln  Gln  Arg  Ala  Ala  Pro  Gly  Ser  Gln  Asn  Ser  Asp  Ser  Arg  Ala
               915                      920                      925

Ser  Phe  Gln  Ser  Xaa  Phe  Lys  Arg  Lys  Glu  Leu  Ser  Cys  Ser  Ser  Met
          930                      935                      940

Asp  Glu  Asp  Ile  Asn  Asn  Asn  Ile  Ile  Asn  Asn  Asn  Asn  Gly  Gln  Val
     945                      950                      955                           960

Pro  Cys  Ala  Val  Leu  Ser  Ala  Leu
                         965
```

( 2 ) INFORMATION FOR SEQ ID NO:15:

( i ) SEQUENCE CHARACTERISTICS:
        ( A ) LENGTH: 3003 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( x i ) SEQUENCE DESCRIPTION: SEQ ID NO:15:

```
GCGCCCGCCC CGAGAGGGTA GCAGATAGTC CCTCGGAGTC TCCGCCCCAG GGGNATGTGG      60
AGGGTGTCCA CCGATTAGGA TCGGGTCCGA GTGATTGTCN ACGGGGCCCG GAGGGTCCGA     120
ACCTGGAGCN CAGCCTGCAC CCTCCACCAC CCGCCCTTCT GGAATGTCAG AACTAANCCA     180
AGAGACAGGT GCACCGGAAA ATTGTGACTG AGCCTTCTTG GCAGAAGAGA AACTGAGTCA     240
CCAGTCCAGG AACCGCAGGG CTGTTGGCGC TCACCTCGAG TCTTCTGGCT GCTTTCCTAT     300
TTGCTCCCTG CAGGCTCCCC CTGTCCTCCT CCTGGGGCAC ATCATGAATG GTGCCCCTTC     360
CCCAGAGGAT GGGGTTTTCC CTTCTCCACC AGCGCTGCCA CCACCCCCTC CCCCAAGTTG     420
GCAAGAGTTC TGTGAGTCCC ATGCGAGGGC TGCTGCCCTG GATCTTGCTC GCCGTTTTCG     480
CCTCTATCTG GCCTCCCACC CACAATATGC AGAGCCGGGA GCAGAGGCTG CCTTTTCTGG     540
CCGTTTTGCT GAGCTCTTCC TGCAGCACTT CGAAGCTGAG GTGGCTCGGG CCTCGGGCTC     600
ACTCTCCCCA CCTGTCTTGG CTCCATTGAG CCCTGGTGTG GAAATCCCAC CATCACATGA     660
CCTGTCCCTT GAGAGCTGCA GGGTGGGTGG GCCCCTGGCA GTGTTGGGCC CTTCTCGATC     720
TTCTGAGGAC CTGGCTGGNC CCCTTCCTTC CTCAGTCTCT TCCTCTACAA CGTCCTCAAA     780
GCCGAAGCTC AAGAAACGCT TCTCCCTCCG CTCGGTGGGT CGTTCAGTCA GAGGTTCTGT     840
CCGAGGCATC CTGCAGTGGC GGGGGGCTGT TGAATCTCCC TCCCAAGCTG GCCTCTGGA     900
GACCACATCA GGTCCTCCAG TTCTAGGTGG AAACAGCAAC TCCAACTCCT CTGGTGGTGC     960
TGGGACAGTT GGTAGGGCAT TGGCCAACGA TGGCACATCC CCTGGGGAGA GATGGACTCA    1020
TCGCTTTGAG AGGCTAAGGC TAAGTCGTGG AGGGGGAACC TTGAGAGACG GAGCAGGAGT    1080
GATACAGAGA GAAGAGCTGC TGAGTTTCAT GGGGGCTGAA GAGGCTGCCC CTGACCCAGC    1140
AGGAGTAGGT CGTGGAGGAG GGGCAGCTGG GCTGACCTCG GGAGGAGGAG GGCAGCCTCA    1200
GTGGCAGAAA TGTCGATTAC TGCTCCGGAG TGAAGGAGAA GGAGGAGGAG GAAGTCGCTT    1260
GGAGTTCTTT GTACCACCCA AGGCATCCCG GCCCCGTCTT AGCATTCCCT GTTCTACTAT    1320
TACTGATGTC CGCACAGCCA CAGCCCTGGA GATGCCTGAC AGGGAGAACA CGTTTGTGGT    1380
TAAGGTAGAA GGCCCTTCAG AGTACATCCT GGAGACAACT GATGCACTTC ATGTGAAGGC    1440
CTGGGTGTCT GACATCCAAG AGTGCCTAAG CCCAGGACCC TGCCCTGCTA TCAGCCCCCG    1500
TCCCATGACC CTTCCCCTGG CCCCTGGGAC CTCCTTCCTC ACAAAGGATA ACACAGAGAG    1560
CCTGGAGTTG CCCTGCCTGA ATCATTCAGA GAGTCTGCCT AGCCAGGATC TTCTTCTGGG    1620
ACCCAGCGAG AGTAACGACC GCCTGTCGCA GGGAGCTTAT GGAGGCCTCT CAGACCGGCC    1680
GTCAGCGTCC TTCTCCCCTA GTTCTGCCTC CATTGCTGCT TCCCATTTTG ACTCAATGGA    1740
ACTGCTTCCT CCAGAGTTGC CCCCTCGGAT TCCCATTGAG GAGGGGCCTC AGCAGGGAC    1800
AGTTCATCCC CTCTCTACCC CGTACCCTCC CCTGGATACT CCTGAAGCAG CCACAGGGTC    1860
ATTCCTCTTT CAAGGGGAGG CAGAGGGGGG TGAGGGGGAC CAGCCCCTCT CAGGCTACCC    1920
```

```
TTGGTTCCAC  GGCATGCTCT  CTCGGCTCAA  AGCTGCCCAG  TTAGTGTTAG  AAGGAGGTAC   1980

CAGCTCCCAT  GGTGTCTTCT  TGGTACGCCA  GAGTGAGACA  AGACGTGGTG  AATATGTCCT   2040

CACTTTCAAC  TTCCAGGGCA  AGGCTAAGCA  CCTGCGTTTG  TCACTAAATG  AGGAGGGTCA   2100

GTGCCGGGTC  CAACATCTGT  GGTTCCAGTC  CATTTCGAT   ATGCTGAGC   ACTTCCGGGT   2160

GCACCCCATC  CCTCTGGAGT  CTGGAGGCTC  CAGTGATGTT  GTCCTTGTCA  GCTATGTGCC   2220

CTCCCAGCGG  CAGCAGGAAC  GGAGCACCTC  CCGTGATCCA  ACCCAGCCCT  CTGAACCCCC   2280

TCCATGGACA  GATCCCCCAC  ATCCTGGGGC  AGAAGAGGCG  TCGGGGGCGC  CAGAAGTGGC   2340

GGCAGCCACA  GCCGCAGCAG  CCAAAGAGAG  GCAAGAGAAG  GAGAAAGCGG  GCGGCGGAGG   2400

GGTCCAGGAA  GAGCTGGTCC  CCATGGCTGA  GCTGGTCCCC  ATGGCTGAAT  GGAAGAGGC    2460

CATAGCACCA  GGCACTGAGG  CTCAGGGTGG  TGCTGGCTCT  AGTGGGGACT  TGGAGGTGTC   2520

CCTAATGGTT  CAGCTCCAGC  AGTTACCACT  AGGGGGCAAC  GGAGAAGAAG  GGGGTCACCC   2580

CCGAGCCATT  AATAACCAGT  ACTCATTTGT  CTGAGATACC  TGCCCACCCT  CCATTTCCT    2640

GCTCCCAGCC  TTAAGTTGTG  AGACTGGGCT  GGGTAAGGAC  ACAGAGGAAA  GTGGGAGTCC   2700

CCTCCCTACA  TGCTTCCTGA  CCCTTGTCAG  CCAAGGGTGT  GTATGTTGGT  ACAAGTAGAG   2760

GTTCAAGAGC  CCAGTTAAGT  CCCCAGTTAC  TACACTACAG  GTGCCCTTGC  CCCGAGGCCA   2820

AGGACTTGGG  CTCCATTACC  TCCCTGAGGG  GCTCTTATGG  TCAGCCCCAT  CCCTGGGGC    2880

TGTTTCCCCC  NCTAATAACC  CCCAACCCAA  GCAAGGGTGA  GGGGGAAGGG  CTGTCAGTTA   2940

TATTAAGGTT  GTTGTTGTTG  TTTTAAACNA  AATGGAAAAG  CATAAATAAA  TAAAGGGTTT   3000

ATC                                                                     3003
```

( 2 ) INFORMATION FOR SEQ ID NO:16:

( i ) SEQUENCE CHARACTERISTICS:
        ( A ) LENGTH: 756 amino acids
        ( B ) TYPE: amino acid
        ( C ) STRANDEDNESS: Not Relevant
        ( D ) TOPOLOGY: Not Relevant ( i i ) MOLECULE TYPE: protein ( x i ) SEQUENCE DESCRIPTION: SEQ ID NO:16:

```
Met Asn Gly Ala Pro Ser Pro Glu Asp Gly Val Phe Pro Ser Pro Pro
 1               5                  10                  15

Ala Leu Pro Pro Pro Pro Pro Ser Trp Gln Glu Phe Cys Glu Ser
             20                  25                  30

His Ala Arg Ala Ala Ala Leu Asp Leu Ala Arg Arg Phe Arg Leu Tyr
             35                  40                  45

Leu Ala Ser His Pro Gln Tyr Ala Glu Pro Gly Ala Glu Ala Ala Phe
         50                  55                  60

Ser Gly Arg Phe Ala Glu Leu Phe Leu Gln His Phe Glu Ala Glu Val
65                   70                  75                  80

Ala Arg Ala Ser Gly Ser Leu Ser Pro Val Leu Ala Pro Leu Ser
                 85                  90                  95

Pro Gly Val Glu Ile Pro Pro Ser His Asp Leu Ser Leu Glu Ser Cys
                100                 105                 110

Arg Val Gly Gly Pro Leu Ala Val Leu Gly Pro Ser Arg Ser Ser Glu
            115                 120                 125

Asp Leu Ala Gly Pro Leu Pro Ser Ser Val Ser Ser Thr Thr Ser
        130                 135                 140

Ser Lys Pro Lys Leu Lys Lys Arg Phe Ser Leu Arg Ser Val Gly Arg
```

| 145 | | | | 150 | | | | 155 | | | | 160 | | | |
|---|---|---|---|---|---|---|---|---|---|---|---|---|---|---|---|
| Ser | Val | Arg | Gly | Ser | Val | Arg | Gly | Ile | Leu | Gln | Trp | Arg | Gly | Ala | Val |
| | | | | 165 | | | | 170 | | | | 175 | | | |
| Glu | Ser | Pro | Ser | Gln | Ala | Gly | Pro | Leu | Glu | Thr | Thr | Ser | Gly | Pro | Pro |
| | | | 180 | | | | 185 | | | | | 190 | | | |
| Val | Leu | Gly | Gly | Asn | Ser | Asn | Asn | Ser | Ser | Gly | Gly | Ala | Gly | Thr | |
| | | | 195 | | | | 200 | | | | 205 | | | | |
| Val | Gly | Arg | Ala | Leu | Ala | Asn | Asp | Gly | Thr | Ser | Pro | Gly | Glu | Arg | Trp |
| | 210 | | | | | 215 | | | | | 220 | | | | |
| Thr | His | Arg | Phe | Glu | Arg | Leu | Arg | Leu | Ser | Arg | Gly | Gly | Gly | Thr | Leu |
| 225 | | | | | 230 | | | | | 235 | | | | | 240 |
| Arg | Asp | Gly | Ala | Gly | Val | Ile | Gln | Arg | Glu | Glu | Leu | Leu | Ser | Phe | Met |
| | | | | 245 | | | | | 250 | | | | | 255 | |
| Gly | Ala | Glu | Glu | Ala | Ala | Pro | Asp | Pro | Ala | Gly | Val | Gly | Arg | Gly | Gly |
| | | | 260 | | | | | 265 | | | | | 270 | | |
| Gly | Ala | Ala | Gly | Leu | Thr | Ser | Gly | Gly | Gly | Gln | Pro | Gln | Trp | Gln | |
| | | 275 | | | | | 280 | | | | | 285 | | | |
| Lys | Cys | Arg | Leu | Leu | Leu | Arg | Ser | Glu | Gly | Glu | Gly | Gly | Gly | Gly | Ser |
| | 290 | | | | | 295 | | | | | 300 | | | | |
| Arg | Leu | Glu | Phe | Phe | Val | Pro | Pro | Lys | Ala | Ser | Arg | Pro | Arg | Leu | Ser |
| 305 | | | | | 310 | | | | | 315 | | | | | 320 |
| Ile | Pro | Cys | Ser | Thr | Ile | Thr | Asp | Val | Arg | Thr | Ala | Thr | Ala | Leu | Glu |
| | | | | 325 | | | | | 330 | | | | | 335 | |
| Met | Pro | Asp | Arg | Glu | Asn | Thr | Phe | Val | Val | Lys | Val | Glu | Gly | Pro | Ser |
| | | | 340 | | | | | 345 | | | | | 350 | | |
| Glu | Tyr | Ile | Leu | Glu | Thr | Thr | Asp | Ala | Leu | His | Val | Lys | Ala | Trp | Val |
| | | | 355 | | | | | 360 | | | | | 365 | | |
| Ser | Asp | Ile | Gln | Glu | Cys | Leu | Ser | Pro | Gly | Pro | Cys | Pro | Ala | Ile | Ser |
| | 370 | | | | | 375 | | | | | 380 | | | | |
| Pro | Arg | Pro | Met | Thr | Leu | Pro | Leu | Ala | Pro | Gly | Thr | Ser | Phe | Leu | Thr |
| 385 | | | | | 390 | | | | | 395 | | | | | 400 |
| Lys | Asp | Asn | Thr | Glu | Ser | Leu | Glu | Leu | Pro | Cys | Leu | Asn | His | Ser | Glu |
| | | | | 405 | | | | | 410 | | | | | 415 | |
| Ser | Leu | Pro | Ser | Gln | Asp | Leu | Leu | Leu | Gly | Pro | Ser | Glu | Ser | Asn | Asp |
| | | | 420 | | | | | 425 | | | | | 430 | | |
| Arg | Leu | Ser | Gln | Gly | Ala | Tyr | Gly | Gly | Leu | Ser | Asp | Arg | Pro | Ser | Ala |
| | | 435 | | | | | 440 | | | | | 445 | | | |
| Ser | Phe | Ser | Pro | Ser | Ser | Ala | Ser | Ile | Ala | Ala | Ser | His | Phe | Asp | Ser |
| | 450 | | | | | 455 | | | | | 460 | | | | |
| Met | Glu | Leu | Leu | Pro | Pro | Glu | Leu | Pro | Pro | Arg | Ile | Pro | Ile | Glu | Glu |
| 465 | | | | | 470 | | | | | 475 | | | | | 480 |
| Gly | Pro | Pro | Ala | Gly | Thr | Val | His | Pro | Leu | Ser | Thr | Pro | Tyr | Pro | Pro |
| | | | | 485 | | | | | 490 | | | | | 495 | |
| Leu | Asp | Thr | Pro | Glu | Ala | Ala | Thr | Gly | Ser | Phe | Leu | Phe | Gln | Gly | Glu |
| | | | 500 | | | | | 505 | | | | | 510 | | |
| Ala | Glu | Gly | Gly | Glu | Gly | Asp | Gln | Pro | Leu | Ser | Gly | Tyr | Pro | Trp | Phe |
| | | | 515 | | | | | 520 | | | | | 525 | | |
| His | Gly | Met | Leu | Ser | Arg | Leu | Lys | Ala | Ala | Gln | Leu | Val | Leu | Glu | Gly |
| | | 530 | | | | | 535 | | | | | 540 | | | |
| Gly | Thr | Ser | Ser | His | Gly | Val | Phe | Leu | Val | Arg | Gln | Ser | Glu | Thr | Arg |
| 545 | | | | | 550 | | | | | 555 | | | | | 560 |
| Arg | Gly | Glu | Tyr | Val | Leu | Thr | Phe | Asn | Phe | Gln | Gly | Lys | Ala | Lys | His |
| | | | | 565 | | | | | 570 | | | | | 575 | |

-continued

| | | | | | | | | | | | | | | |
|---|---|---|---|---|---|---|---|---|---|---|---|---|---|---|
| Leu | Arg | Leu | Ser 580 | Leu | Asn | Glu | Glu | Gly 585 | Gln | Cys | Arg | Val | Gln 590 | His | Leu |
| Trp | Phe | Gln 595 | Ser | Ile | Phe | Asp | Met 600 | Leu | Glu | His | Phe | Arg 605 | Val | His | Pro |
| Ile | Pro 610 | Leu | Glu | Ser | Gly | Gly 615 | Ser | Ser | Asp | Val | Val 620 | Leu | Val | Ser | Tyr |
| Val 625 | Pro | Ser | Gln | Arg | Gln 630 | Gln | Glu | Arg | Ser | Thr 635 | Ser | Arg | Asp | Pro | Thr 640 |
| Gln | Pro | Ser | Glu | Pro 645 | Pro | Pro | Trp | Thr | Asp 650 | Pro | Pro | His | Pro | Gly 655 | Ala |
| Glu | Glu | Ala | Ser 660 | Gly | Ala | Pro | Glu | Val 665 | Ala | Ala | Ala | Thr | Ala 670 | Ala | Ala |
| Ala | Lys | Glu 675 | Arg | Gln | Glu | Lys | Glu 680 | Lys | Ala | Gly | Gly | Gly 685 | Gly | Val | Gln |
| Glu | Glu 690 | Leu | Val | Pro | Met | Ala 695 | Glu | Leu | Val | Pro | Met 700 | Ala | Glu | Leu | Glu |
| Glu 705 | Ala | Ile | Ala | Pro | Gly 710 | Thr | Glu | Ala | Gln | Gly 715 | Gly | Ala | Gly | Ser | Ser 720 |
| Gly | Asp | Leu | Glu | Val 725 | Ser | Leu | Met | Val | Gln 730 | Leu | Gln | Gln | Leu | Pro 735 | Leu |
| Gly | Gly | Asn | Gly 740 | Glu | Glu | Gly | Gly | His 745 | Pro | Arg | Ala | Ile | Asn 750 | Asn | Gln |
| Tyr | Ser | Phe 755 | Val | | | | | | | | | | | | |